(12) United States Patent
Fuerst et al.

(10) Patent No.: US 12,161,419 B2
(45) Date of Patent: Dec. 10, 2024

(54) ROBOT-ASSISTED SETUP FOR A SURGICAL ROBOTIC SYSTEM

(71) Applicant: Verb Surgical Inc., Santa Clara, CA (US)

(72) Inventors: Bernhard Adolf Fuerst, Sunnyvale, CA (US); Eric Mark Johnson, Half Moon Bay, CA (US)

(73) Assignee: Verb Surgical Inc., Santa Clara, CA (US)

( * ) Notice: Subject to any disclaimer, the term of this patent is extended or adjusted under 35 U.S.C. 154(b) by 889 days.

(21) Appl. No.: 17/194,074

(22) Filed: Mar. 5, 2021

(65) Prior Publication Data

US 2022/0280238 A1 Sep. 8, 2022

(51) Int. Cl.
| | | |
|---|---|---|
| A61B 34/10 | (2016.01) | |
| A61B 17/34 | (2006.01) | |
| A61B 34/00 | (2016.01) | |
| A61B 34/32 | (2016.01) | |
| A61B 90/00 | (2016.01) | |

(Continued)

(52) U.S. Cl.
CPC .......... *A61B 34/10* (2016.02); *A61B 17/3468* (2013.01); *A61B 34/32* (2016.02); *A61B 34/74* (2016.02); *A61B 90/37* (2016.02); *A61G 13/101* (2013.01); *A61B 2034/104* (2016.02); *A61B 2034/107* (2016.02); *A61B 2034/303* (2016.02)

(58) Field of Classification Search
CPC ..... A61B 34/10; A61B 17/3468; A61B 34/32; A61B 34/74; A61B 90/37; A61B 2034/104; A61B 2034/107; A61B 2034/303; A61B 34/37; A61B 2034/302; A61B 34/20; A61B 34/25; A61B 34/30; A61B 2090/064; A61B 2034/2048; A61B 2090/371; A61B 90/361; A61B 17/34; A61G 13/101

See application file for complete search history.

(56) References Cited

U.S. PATENT DOCUMENTS 9,259,282 B2 * 2/2016 Azizian ................. A61B 34/30
9,956,044 B2 * 5/2018 Gomez ................. A61B 34/76
(Continued)

FOREIGN PATENT DOCUMENTS

| WO | 2020016864 A2 | 1/2020 |
| WO | 2020140048 A1 | 7/2020 |
| WO | 2020176113 A1 | 9/2020 |

OTHER PUBLICATIONS

Dong et al., Robust trocar detection and localization during robot-assisted endoscopic surgery, 2016 IEEE International Conference on Robotics and Automation, pp. 4109-4114 (Year: 2016).*

(Continued)

*Primary Examiner* — Sze-Hon Kong
(74) *Attorney, Agent, or Firm* — Aikin & Gallant, LLP

(57) ABSTRACT

A method performed by a surgical robotic system. The method determines a surgical procedure that is to be performed using a robotic arm. The method determines, for the robotic arm, a planned trajectory based on the surgical procedure, where the planned trajectory is from a current pose of the robotic arm to a predefined procedure pose that is within a threshold distance from a trocar that is coupled to a patient. The method drives the robotic arm along the planned trajectory from the current pose to the predefined procedure pose.

35 Claims, 12 Drawing Sheets

(51) Int. Cl.
*A61G 13/10* (2006.01)
*A61B 34/30* (2016.01)

(56) References Cited

U.S. PATENT DOCUMENTS

| | | | |
|---|---|---|---|
| 10,441,294 B2* | 10/2019 | Lavallee | B25J 9/0009 |
| 10,661,453 B2* | 5/2020 | Koenig | B25J 13/02 |
| 11,801,605 B2* | 10/2023 | Fredrickson | B25J 19/023 |
| 11,844,574 B2* | 12/2023 | VanDyken | A61B 34/30 |
| 11,850,010 B2* | 12/2023 | Moctezuma de la Barrera | G02B 27/017 |
| 2010/0174410 A1* | 7/2010 | Greer | A61B 34/37 700/264 |
| 2014/0005684 A1* | 1/2014 | Kim | A61B 34/76 606/130 |
| 2016/0314710 A1* | 10/2016 | Jarc | G09B 23/28 |
| 2016/0361122 A1 | 12/2016 | Seeber | |
| 2017/0143429 A1* | 5/2017 | Richmond | A61B 34/37 |
| 2017/0189127 A1 | 7/2017 | Weir | |
| 2017/0252921 A1* | 9/2017 | Hynna | A61B 90/98 |
| 2018/0080841 A1* | 3/2018 | Cordoba | A61B 34/35 |
| 2019/0321115 A1 | 10/2019 | Anderson et al. | |
| 2020/0268460 A1* | 8/2020 | Tse | A61B 34/30 |
| 2020/0315721 A1* | 10/2020 | Rabindran | A61B 90/03 |
| 2021/0077203 A1* | 3/2021 | Monteverde | B25J 9/1633 |
| 2021/0121253 A1* | 4/2021 | Leibrandt | A61B 34/76 |
| 2021/0153966 A1* | 5/2021 | Lau | A61B 46/10 |
| 2021/0196383 A1* | 7/2021 | Shelton, IV | G16H 20/40 |
| 2021/0205032 A1* | 7/2021 | Saeidi | A61B 34/25 |
| 2021/0290310 A1* | 9/2021 | Laby | A61B 34/32 |
| 2021/0298846 A1* | 9/2021 | Dozeman | A61B 90/03 |
| 2022/0175471 A1* | 6/2022 | Pickett | A61B 34/30 |
| 2022/0387116 A1* | 12/2022 | Hashimoto | G16H 40/63 |
| 2023/0000565 A1* | 1/2023 | Pickett | A61B 17/0491 |
| 2023/0149105 A1* | 5/2023 | Thornycroft | A61B 90/06 606/45 |
| 2023/0270511 A1* | 8/2023 | Junio | B25J 9/1697 700/248 |

OTHER PUBLICATIONS

Austad et al., Computer-aided planning of trocar placement and robot settings in robot-assisted surgery, International Congress Series 1230 (2001) pp. 1020-1026 (Year: 2001).*

Toti et al., A Smart Trocar for AUtomatic Tool Recognition in Laparoscopic Surgery, 2015, Surgical Innovation, vol. 22(I) pp. 77-82 (Year: 2015).*

Adhami et al., Positioning Tele-Operated Surgical Robots for Collision-Free Optimal Operation, Proceedings of the 2002 IEEE International Conference on Robotics & Automation, May 2002, pp. 2962-2967 (Year: 2002).*

International Search Report and Written Opinion of the International Searching Authority mailed Apr. 22, 2022 for related International Application No. PCT/IB2022/050385.

* cited by examiner

ROBOT-ASSISTED SETUP FOR A SURGICAL ROBOTIC SYSTEM

FIELD

Various aspects of the disclosure relate generally to surgical robotic systems, and more specifically to a surgical robotic system that performs a robot-assisted setup for a surgical procedure. Other aspects are also described.

BACKGROUND

Minimally-invasive surgery, MIS, such as laparoscopic surgery, uses techniques that are intended to reduce tissue damage during a surgical procedure. Laparoscopic procedures typically call for creating a number of small incisions in the patient, e.g., in the abdomen, through which several surgical tools such as an endoscope, a blade, a grasper, and a needle, are then inserted into the patient. A gas is injected into the abdomen which insufflates the abdomen thereby providing more space around the tips of the tools, making it easier for the surgeon to see (via the endoscope) and manipulate tissue at the surgical site. MIS can be performed faster and with less surgeon fatigue using a surgical robotic system in which the surgical tools are operatively attached to the distal ends of robotic arms, and a control system actuates the arm and its attached tool. The tip of the tool will mimic the position and orientation movements of a handheld user input device (UID) as the latter is being manipulated by the surgeon. The surgical robotic system may have multiple surgical arms, one or more of which has an attached endoscope and others have attached surgical instruments for performing certain surgical actions.

Control inputs from a user (e.g., surgeon or other operator) are captured via one or more user input devices and then translated into control of the robotic system. For example, in response to user commands, a tool drive having one or more motors may actuate one or more degrees of freedom of a surgical tool when the surgical tool is positioned at the surgical site in the patient.

SUMMARY

In MIS procedures, an operator manually performs a pre-operation robotic arm setup to maneuver and orientate one or more robotic arms that are to be used during a surgical procedure such that surgical tools (e.g., coupled to distal ends) of the robotic arms are positioned close to where the surgical tools are inserted into the patient. First, a patient is prepped and laid on a surgical table. At this point, the robotic arms may be in a stowed configuration in which the arms are stowed under the surgical table in order for the patient and operators to access the table. Once the patient is on the table, the operator manually extends each of the robotic arms from its stowed position for sterile draping, e.g., covering one or more portions of the arms with a sterile barrier. After draping, the arms can be partially retracted and positioned to one side until needed for use. A number of conventional laparoscopic steps may then be performed including trocar placement into the patient's body and insufflation. For example, each trocar can be inserted with the aid of an obturator, into a small incision and through the body wall. Once a distal end of a cannula of the trocar is properly positioned and inserted through tissue and into an interior region of the patient, for example, through the abdominal wall of the patient, a surgical arm having a trocar docking interface at its distal end, or a tool drive attached thereto, is manually maneuvered by the operator until the trocar docking interface is proximate to and aligned with an attachment portion (e.g., a mating interface) on the proximal end of the trocar (outside the patient.) The operator then (e.g., manually) latches the trocar docking interface to the mating interface of the trocar, thereby rigidly attaching the arm to the trocar. A surgical tool having an end effector at its distal end (e.g., scissors, grasping jaws, or camera) is then inserted into a top opening of the cannula and the tool is then attached to the arm such that further surgical operations can be performed with the tool. Depending on how many trocars and robotic arms are needed for the surgical procedure, the operator may perform these steps several times to position and latch several surgical arms to corresponding trocars.

These initial manual robotic arm setup tasks require a significant amount of time and are prone to human error. For example, an operator may spend at least twenty minutes to successfully manually setup each of several robotic arms for the surgical procedure. If, however, an operator fails to correctly position one or more of the robotic arms more time may be required to perform readjustments of the arms. In addition, manually moving and manipulating robotic arms may result in collisions between arms, the patient, the table, and other accessories (or objects) within an operating room. As a result, there is a need for a robot-assisted setup that effectively and efficiently positions and orientates robotic arms.

The present disclosure provides a robot-assisted setup process of a surgical robotic system that automatically (e.g., without user intervention) positions and orientates one or more robotic arms for a surgical procedure. The system determines a surgical procedure that is to be performed using one or more (e.g., four) robotic arms. For instance, the system may receive a user selection of a graphical user interface (GUI) item of several GUI items, each associated with a different surgical procedure (e.g., a gastrectomy, a gastric bypass, a cholecystectomy, etc.) and displayed on a display screen of the system. For each of the robotic arms, the system determines a planned trajectory based on the surgical procedure, the planned trajectory being from a current pose (position and/or orientation) of the robotic arm to a (predefined) "procedure" pose in which a docking interface of the robotic arm is at or within a threshold distance from a corresponding trocar, and from which an operator of the surgical robotic system is to manually guide the robotic arm to couple to a trocar. As an example, the system may perform a table lookup into a data structure that associates each of several surgical procedures with one or more planned trajectories for one or more robotic arms. For example, to perform a gastric bypass two robotic arms may be used, in which case the data structure may associate one planned trajectory for one of the robotic arms and may associate another planned trajectory for the other robotic arm. Planned trajectories may include predefined paths along which the robotic arm moves and no portion of the robotic arm comes into contact with 1) at least 95% of patients who may be positioned on the table for the surgical procedure and 2) other robotic arms. The planned trajectories may also account for objects within a range of motion of the robotic arm such that the robotic arm does not collide with the objects while being moved (or guided) along the planned trajectory. For instance, a planned trajectory may account for an arm rest, which may extend away from the surgical table regardless of whether or not the arm rest is being used for this particular procedure. The system then guides each of the robotic arms (e.g., consecutively or simultaneously) along the planned trajectory from its current pose to the predefined procedure pose. As a result, the system efficiently and successfully positions and orientates the robotic arms while reducing setup time (e.g., from twenty minutes to three minutes) and without any (potential) collisions.

In one aspect, each of the robotic arm's planned trajectory may include at least one intermediate pose at which the robotic arm is paused in a specific (predefined) position and orientation. For example, one intermediate pose may be a "preparation" pose in which a configuration of the robotic arms that maximizes physical and direct access to the patient by the operator (or surgeon). In particular, while robotic arms are in their respective current poses (e.g., poses of the arms before moving along their respective planned trajectories) there may be a first open area between the arms to access the patient. When guiding the arms, the system may move the robotic arms from their respective current poses to intermediate poses in which there is a second open area between the arms to access the patient that is larger than the first open area, and the system may pause the robotic arms at their respective intermediate poses. This second open area may provide the surgeon sufficient access to the patient's body cavity in order to perform one or more surgical tasks, such as inserting trocars into the patient before the arms are positioned to latch to the trocars.

In another aspect, the surgical robotic system may develop the trajectories and/or poses of the robotic arms for later use during (or before) a surgical procedure, as described herein. For instance, the system may identify a surgical procedure in which tool drives coupled to distal ends of several robotic arms are to be positioned about trocars, which are to be placed about and through (e.g., an abdomen of) a patient that is positioned on a surgical table. In particular, an operator may select (e.g., via a user console) the surgical procedure from several surgical procedures. For each arm, the system determines a procedure pose in which a tool drive of the robotic arm is at a position that is less than a threshold distance from each of several positions of a corresponding trocar across several different sized patients. For instance, the procedure pose may be an average pose used across several previously performed surgical procedures at which the robotic arm is docked to a corresponding trocar. The system determines, for each robotic arm, a planned trajectory from an initial pose (e.g., a "stowed" pose) to the procedure pose in which while traversing the planned trajectory the robotic arm avoids contact with other robotic arms, the surgical table, and a patient volume of a patient positioned on the surgical table, where the patient volume accounts for at least 95% of a patient population on which the surgical procedure is performed. In other words, the patient volume may be a patient volume (e.g., size and shape) that is larger than 95% of volumes of the patient population.

The above summary does not include an exhaustive list of all aspects of the disclosure. It is contemplated that the disclosure includes all systems and methods that can be practiced from all suitable combinations of the various aspects summarized above, as well as those disclosed in the Detailed Description below and particularly pointed out in the claims. Such combinations may have particular advantages not specifically recited in the above summary.

BRIEF DESCRIPTION OF THE DRAWINGS

The aspects are illustrated by way of example and not by way of limitation in the figures of the accompanying drawings in which like references indicate similar elements. It should be noted that references to "an" or "one" aspect of this disclosure are not necessarily to the same aspect, and they mean at least one. Also, in the interest of conciseness and reducing the total number of figures, a given figure may be used to illustrate the features of more than one aspect, and not all elements in the figure may be required for a given aspect.

DETAILED DESCRIPTION

Several aspects of the disclosure with reference to the appended drawings are now explained. Whenever the shapes, relative positions and other aspects of the parts described in a given aspect are not explicitly defined, the scope of the disclosure here is not limited only to the parts shown, which are meant merely for the purpose of illustration. Also, while numerous details are set forth, it is understood that some aspects may be practiced without these details. In other instances, well-known circuits, structures, and techniques have not been shown in detail so as not to obscure the understanding of this description. Furthermore, unless the meaning is clearly to the contrary, all ranges set forth herein are deemed to be inclusive of each range's endpoints.

Figure 1:
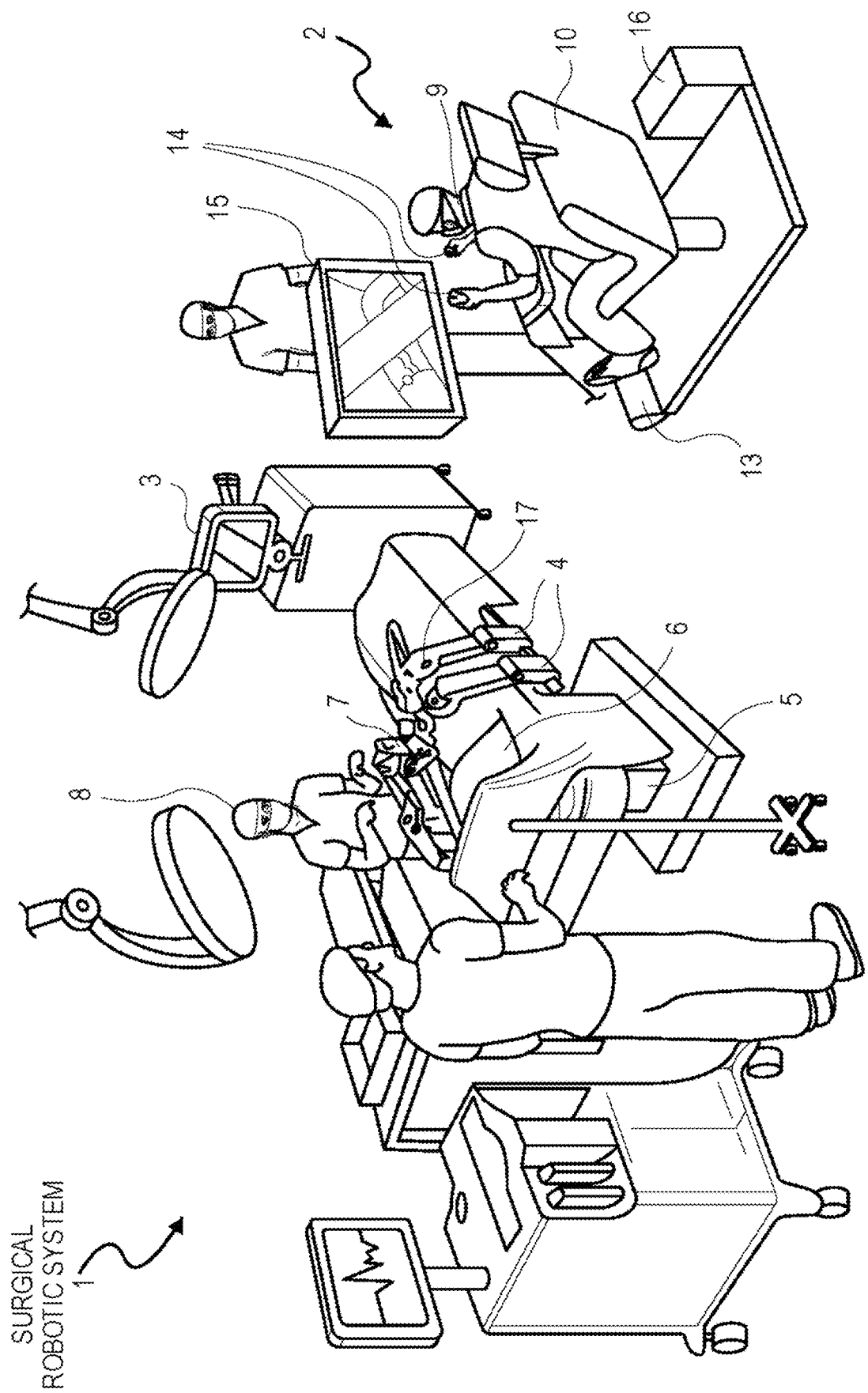
FIG. 1 shows a pictorial view of an example surgical robotic system in an operating arena.

FIG. 1 shows a pictorial view of an example surgical robotic system 1 in an operating arena. The robotic system 1 includes a user console 2, a control tower 3, and one or more surgical robotic arms 4 at a surgical robotic table (surgical table or surgical platform) 5. In one aspect, the arms 4 may be mounted to a table or bed on which the patient rests as shown in the example of FIG. 1. In one aspect, at least some of the arms 4 may be configured differently. For example, at least some of the arms may be mounted on a ceiling, sidewall, or in another suitable structural support, such as a cart separate from the table. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an aspect, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached.

Generally, a remote operator 9, such as a surgeon or other operator, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may include one or more components, such as a seat 10, one or more foot-operated controls (or foot pedals) 13, one or more (handheld) user-input devices (UIDs) 14, and at least one display 15. The display is configured to display, for example, a view of the surgical site inside the patient 6. The display may be configured to display image data (e.g., still images and/or video). In one aspect, the display may be any type of display, such as a liquid crystal display (LCD), a light-emitting diode (LED) display, an organic LED (OLED) display, etc. In some aspects, the display may be a 3D immersive display that is for displaying 3D (surgical) presentations. For instance, during a surgical procedure one or more endoscopic cameras may be capturing image data of a surgical site, which the display presents to the user in 3D. In one aspect, the 3D display may be an autostereoscopic display that provides 3D perception to the user without the need for special glasses. As another example, the 3D display may be a stereoscopic display that provides 3D perception with the use of glasses (e.g., via active shutter or polarized).

In another aspect, the display 15 may be configured to display at last one graphical user interface (GUI) that may provide informative and/or interactive content, to thereby assist a user in performing a surgical procedure with one or more robotic instruments in the surgical robotic system 1. For example, some of the content displayed may include image data captured by one or more endoscopic cameras, as described herein. In another aspect, the GUI may include selectable UI items, which when manipulated by the user may cause the system to perform one or more operations. For instance, the GUI may include a UI item as interactive content to switch control between robotic arms. In one aspect, to interact with the GUI, the system may include input devices, such as a keyboard, a mouse, etc. In another aspect, the user may interact with the GUI using the UID 14. For instance, the user may manipulate the UID to navigate through the GUI, (e.g., with a cursor), and to make a selection may hover the cursor over a UI item and manipulate the UID (e.g., selecting a control or button). In some aspects, the display may be a touch-sensitive display screen. In this case, the user may perform a selection by navigating and selecting through touching the display. In some aspects, any method may be used to navigate and/or select a UI item.

As shown, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. More about these steps is described herein. Next, the surgery proceeds with the remote operator 9 at the user console 2 utilising the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilisation and healthcare record entry or printout via the user console 2.

In one aspect, the remote operator 9 holds and moves the UID 14 to provide an input command to drive (move) one or more robotic arm actuators 17 (or driving mechanism) in the robotic system 1 for teleoperation. The UID 14 may be communicatively coupled to the rest of the robotic system 1, e.g., via a console computer system 16 (or host). The UID 14 can generate spatial state signals corresponding to movement of the UID 14, e.g. position and orientation of the handheld housing of the UID, and the spatial state signals may be input signals to control motions of the robotic arm actuators 17. The robotic system 1 may use control signals derived from the spatial state signals, to control proportional motion of the actuators 17. In one aspect, a console processor of the console computer system 16 receives the spatial state signals and generates the corresponding control signals. Based on these control signals, which control how the actuators 17 are energized to drive a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn drives other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator that opens or closes jaws of the grasper at a distal end of surgical tool 7 to grip tissue within patient 6.

In some aspects, the communication between the surgical robotic table 5 and the user console 2 may be through a control tower 3, which may translate user commands that are received from the user console 2 (and more particularly from the console computer system 16) into robotic control commands that transmitted to the arms 4 on the surgical table 5. The control tower 3 may also transmit status and feedback from the surgical table 5 back to the user console 2. The communication connections between the surgical table 5, the user console 2, and the control tower 3 may be via wired (e.g., optical fiber) and/or wireless links, using any suitable one of a variety of wireless data communication protocols, such as BLUETOOTH protocol. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 7:
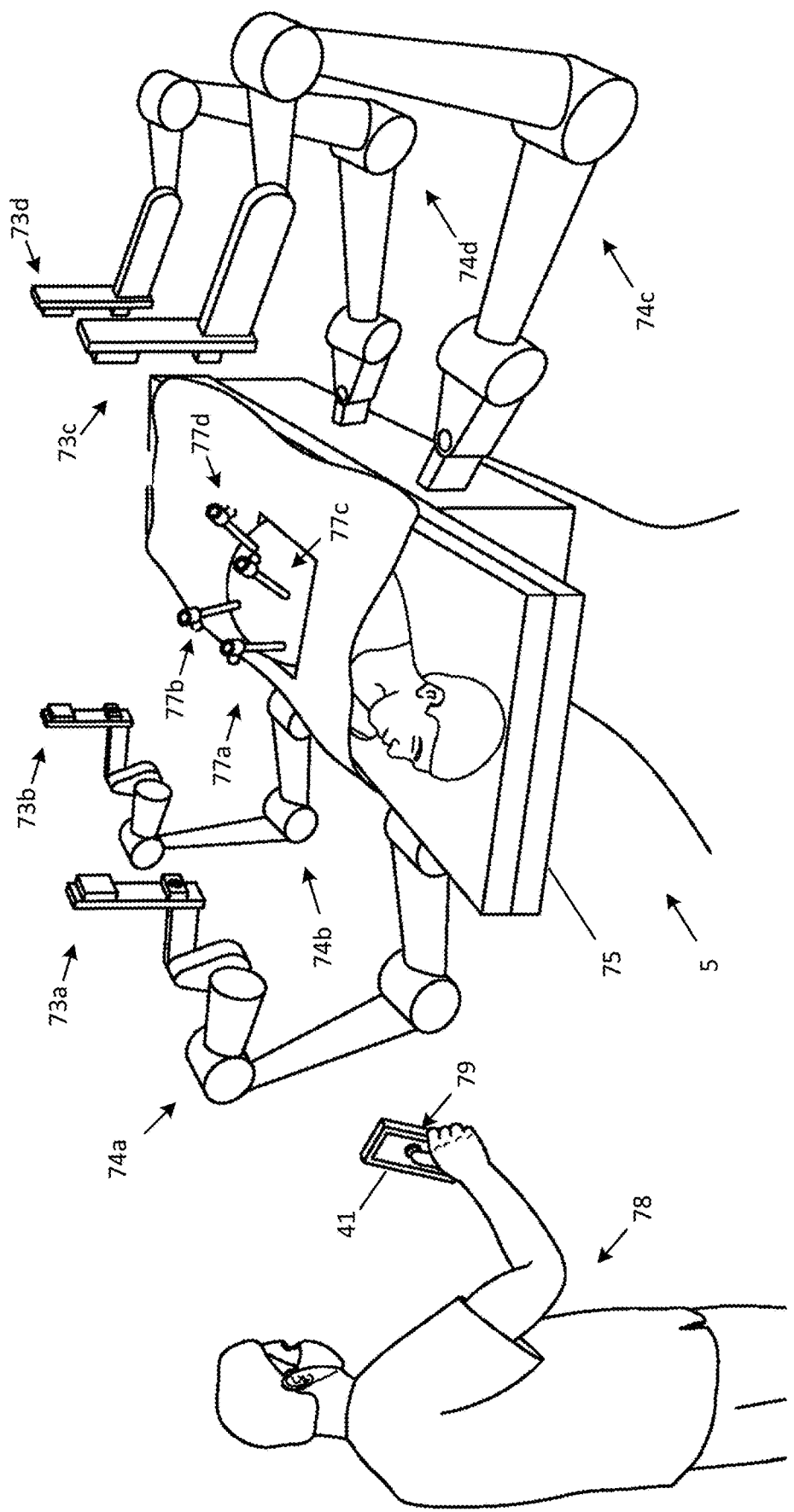
FIGS. 7-10b illustrate various poses of the robotic arms along their respective planned trajectories.

As described herein, to create a port for enabling introduction of a surgical instrument into a patient 6, a trocar assembly (or trocar) may be at least partially inserted into the patient through an incision or entry point in the patient (e.g., in the abdominal wall). In one aspect, the trocar assembly may include a cannula or trocar (e.g., trocar 77a, as shown in FIG. 7), an obturator, and/or a seal. In some variations, the trocar assembly can include an obturator such as a needle with a sharpened tip for penetrating through a patient's skin. The obturator may be disposed within the lumen of the trocar when being inserted into the patient 6, and then removed from the trocar such that a surgical instrument may be inserted through the lumen of the trocar. Once positioned within the body of the patient, the trocar may provide a channel for accessing a body cavity or other site within the patient, for example, such that one or more surgical instruments or tools can be inserted into a body cavity of the patient, as described further herein. It will be understood that a trocar, such as trocar 77a, as described herein includes at least a cannula, and can optionally include an obturator or other components.

Figure 2:
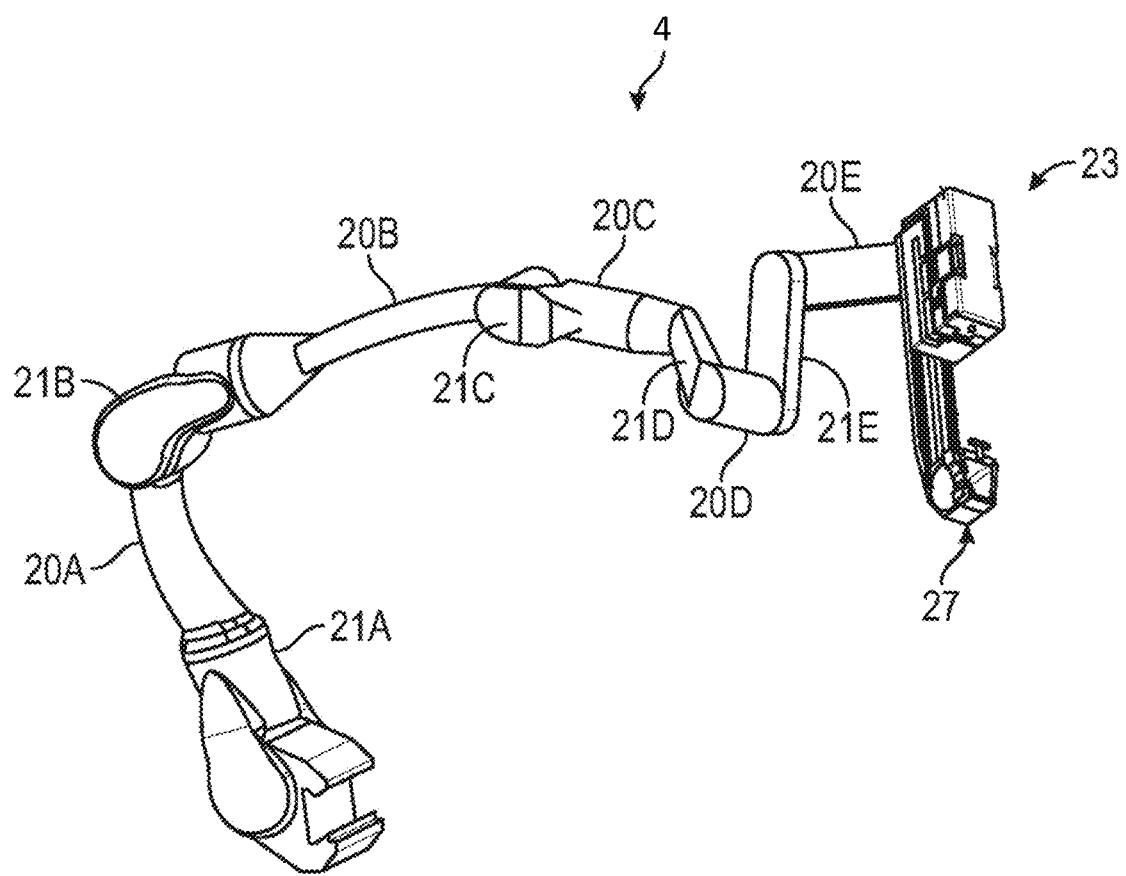
FIG. 2 shows a perspective view of a portion of a robotic arm according to one aspect of the disclosure.

Turning to FIG. 2, a portion of a robotic arm 4 is illustrated according to one aspect of the disclosure. The robotic arm and associated components described herein can form a surgical robotic system according to an aspect of the disclosure. The robotic arm can be incorporated into the surgical robotic system 1, as described herein, or can form a portion of a different system. While a single robotic arm 4 has been illustrated, it will be understood that the robotic arm can include additional arm portions or can be a component of multi-arm apparatus without departing from the disclosure.

The robotic arm 4 includes a plurality of links (e.g., links 20A-20E) and a plurality of joint modules (e.g., joints 21A-21E), where the links are coupled together by the joint modules (or joints), for example link 20B is coupled to link 20C by joint 21C. In one aspect, the joint modules are for actuating the plurality of links relative to one another. The joints can include various joint types, such as a pitch joint or a roll joint, any of which can be actuated manually or by the robotic arm actuators 17, and any of which may substantially constrain the movement of the adjacent links around certain axes relative to others. The robotic arm 4 also includes a tool drive 23 is attached to a distal end of the robotic arm. As described herein, the tool drive 23 can be configured with a docking (or mating) interface 27 to receive an attachment portion (e.g., a mating interface) of a trocar (e.g., such as attachment portion 94 of trocar 77a, as shown in FIG. 10b) such that one or more surgical instruments (e.g., endoscopes, staplers, etc.) can be guided through a lumen of the cannula of the trocar.

The plurality of the joint 21A-21E of the robotic arm can be actuated to position and orient the tool drive 23 for robotic surgeries. In one aspect, the positions (e.g., along X-, Y-, and Z-axes) and rotational orientations (e.g., about the X-, Y-, and Z-axes, e.g., roll, pitch, and yaw) of at least some of the joints and links (e.g., with respect to a reference point, such as the surgical table 5) may define a pose (e.g., a spatial position and orientation) of the robotic arm. In some aspects, a robotic arm's pose may be defined as a set of joint values of one or more of the joints that determines an exact configuration of the robotic arm. In some aspects, as the robotic arm moves (e.g., based on translational and/or rotational movement along at least one of the X-, Y-, and Z-axes), the robotic arm may change between one of several poses. In one aspect, the pose of a robotic arm indicates (or defines) a position and orientation of a portion of the robotic arm. For instance, the pose of the robotic arm may indicate a pose of (e.g., a docking interface 27 of) a tool drive 23 that is coupled to the distal end of the robotic arm.

In one aspect, (e.g., docking interfaces of tool drives that are coupled to) robotic arms of a surgical robotic system are capable of being positioned and orientated in several different poses. At least some poses are illustrated in FIGS. 7-10a. For example, each of these figures illustrates four robotic arms 74a-74b with four tool drives 73a-73d coupled to distal ends of the robotic arms, respectively, while proximal ends of the robotic arms may be coupled to an object, such as the surgical table 5, a (e.g., movable) cart, etc., as described herein. Each figure also includes a patient 6 disposed (or positioned) on top of a table top 75 of the surgical table 5. Inserted into the abdomen of the patient are four trocars 77a-77d.

Figure 8:
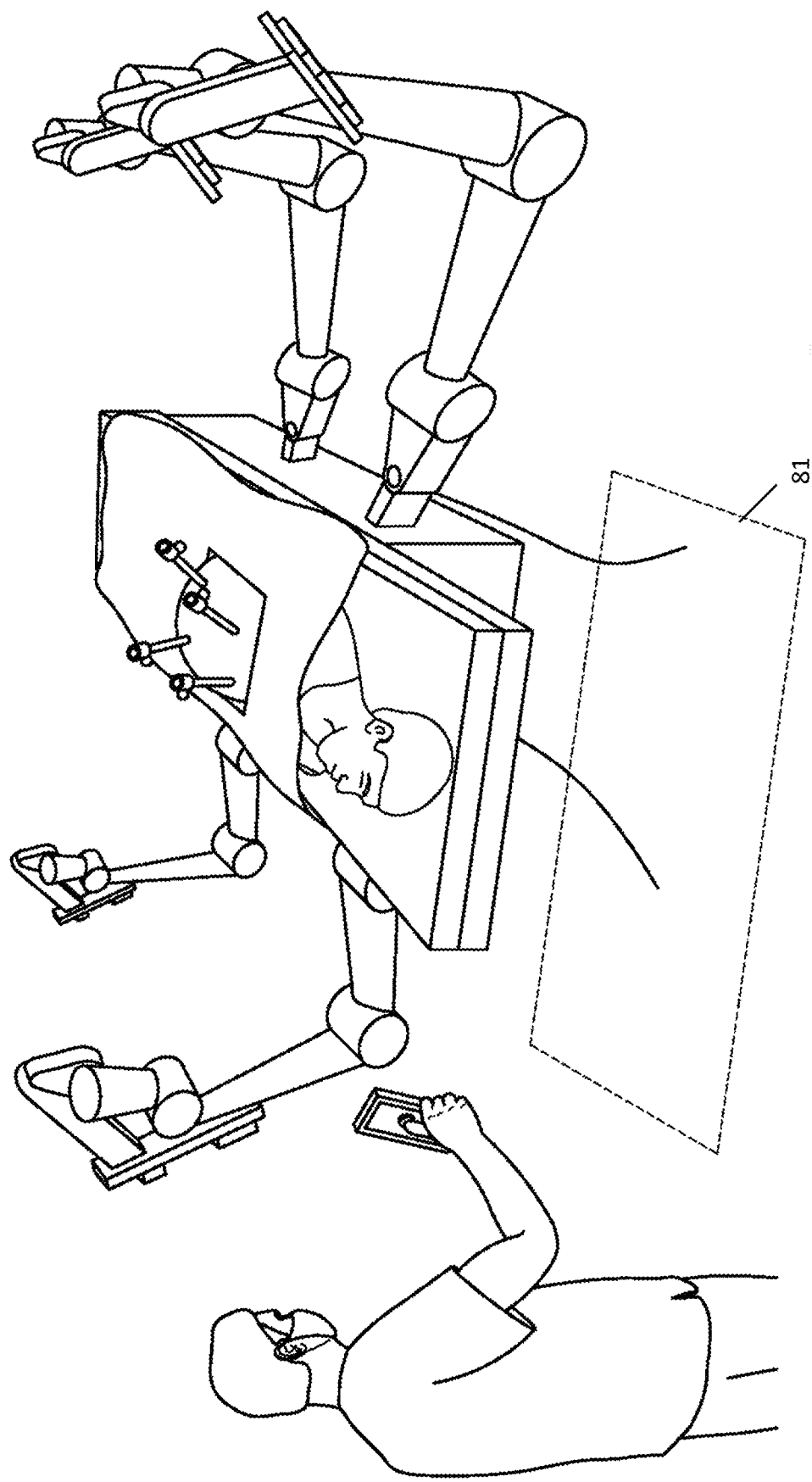

FIG. 7 illustrates each of the robotic arms in a "drape" pose, that is a pose in which an operator 78 may drape at least a portion of each robotic arm with a sterile barrier (not shown) to minimize, inhibit, or prevent the transmission of pathogens. FIG. 8 illustrates each of the robotic arms in a "candle" pose that is a pose in which a distal end of the robotic arm is folded and raised (e.g., with respect to the position of the arms in the drape pose). In one aspect, this pose is defined in order to avoid possible collisions between the robotic arms and other objects during execution of a planned trajectory, for example while the arms traverse respective planned trajectories, as described herein. This figure also illustrates a (first) open area 81 that extends from (or is between) arm 74a and arm 74c that provides room to the operator 78 to access the patient.

Figure 9:
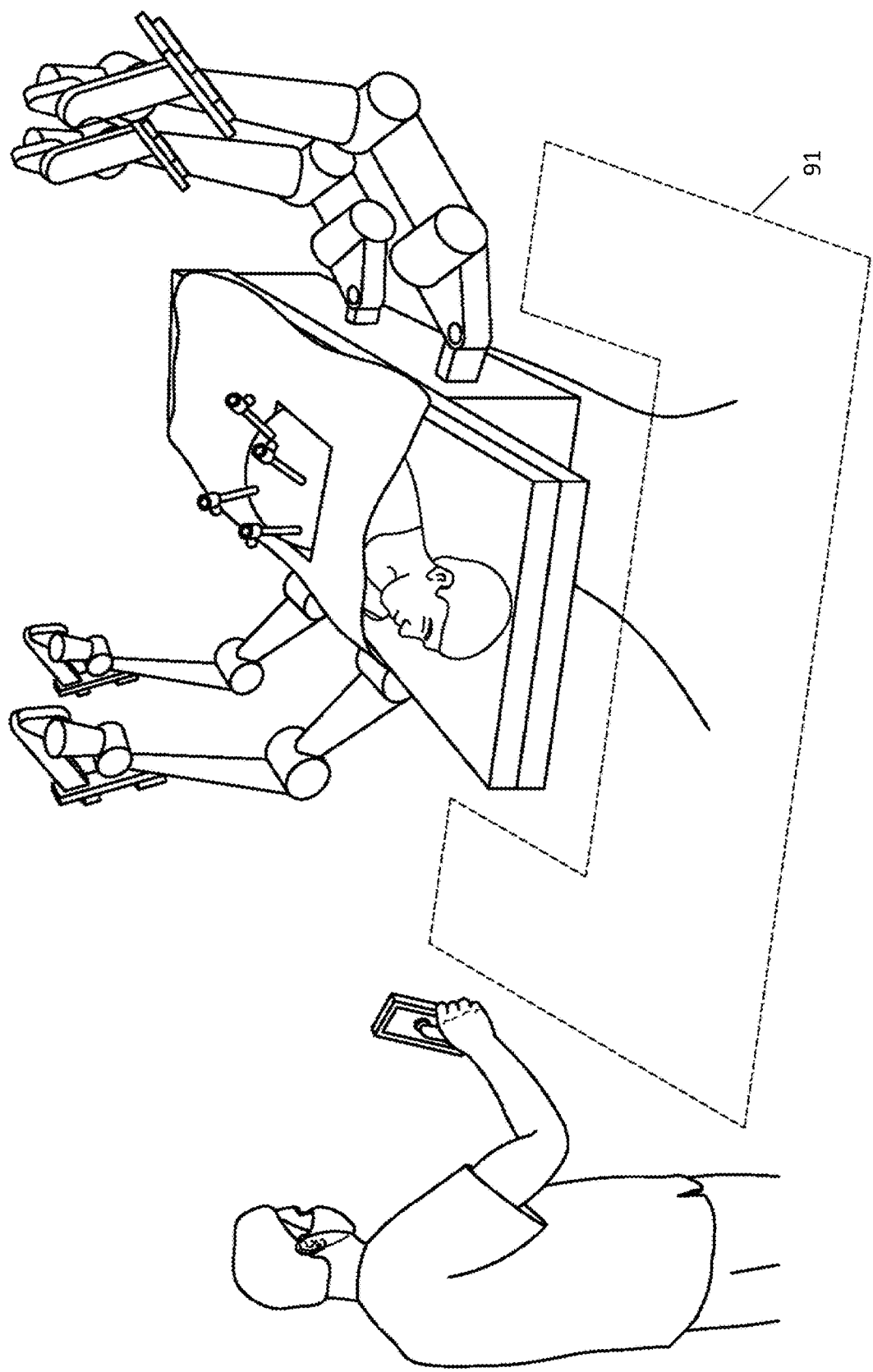

FIG. 9 illustrates each of the robotic arms in a "preparation" pose, that is a pose that maximizes physical and direct access to the patient, while maintaining sterility of the draped robotic arms (which were draped while in the drape pose). For example, this figure shows a (second) open area 91 that is between arm 74a and arm 74c to provide access to the patient that is larger than area 81 illustrated in FIG. 8.

Figure 10A:
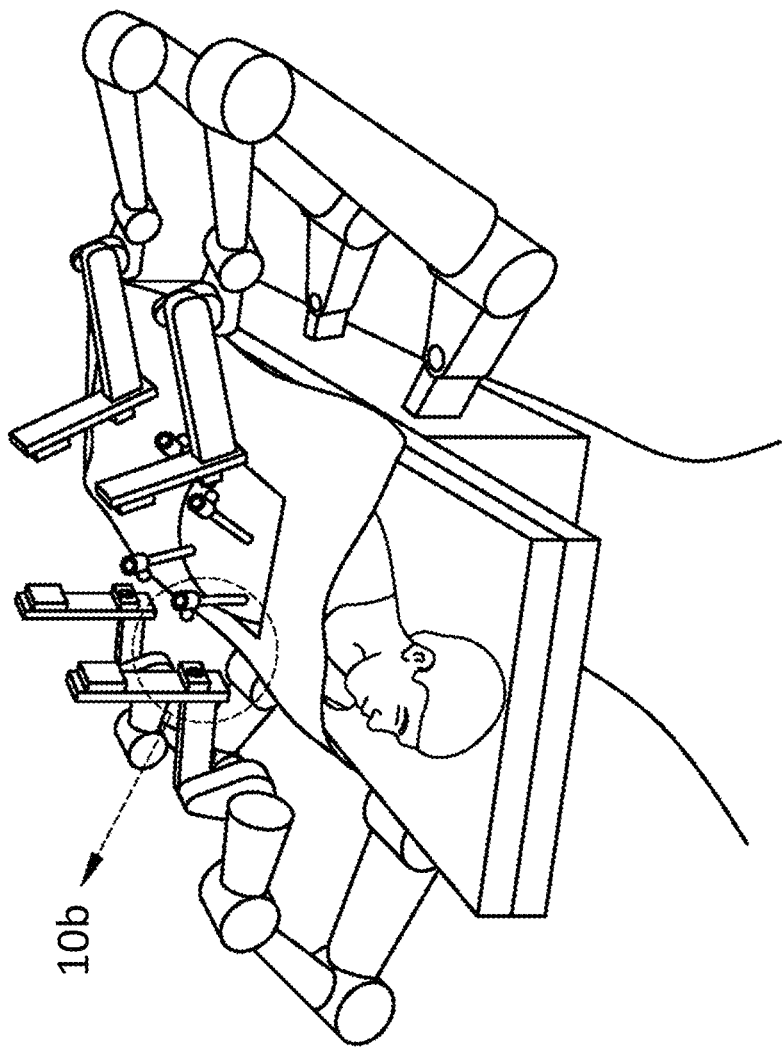
Figure 10A:
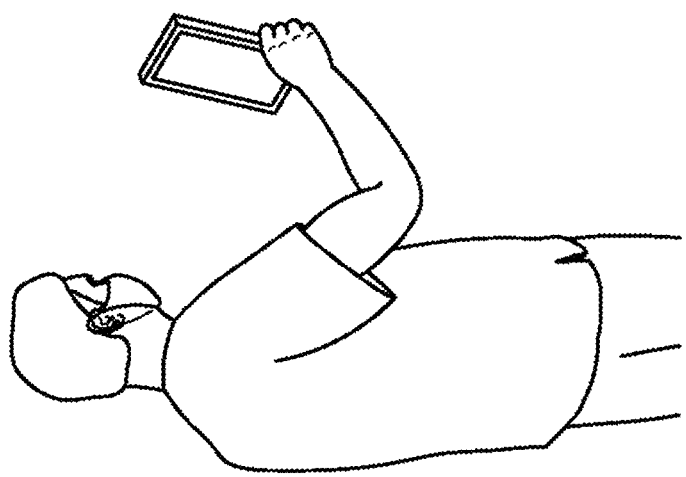
Figure 10B:
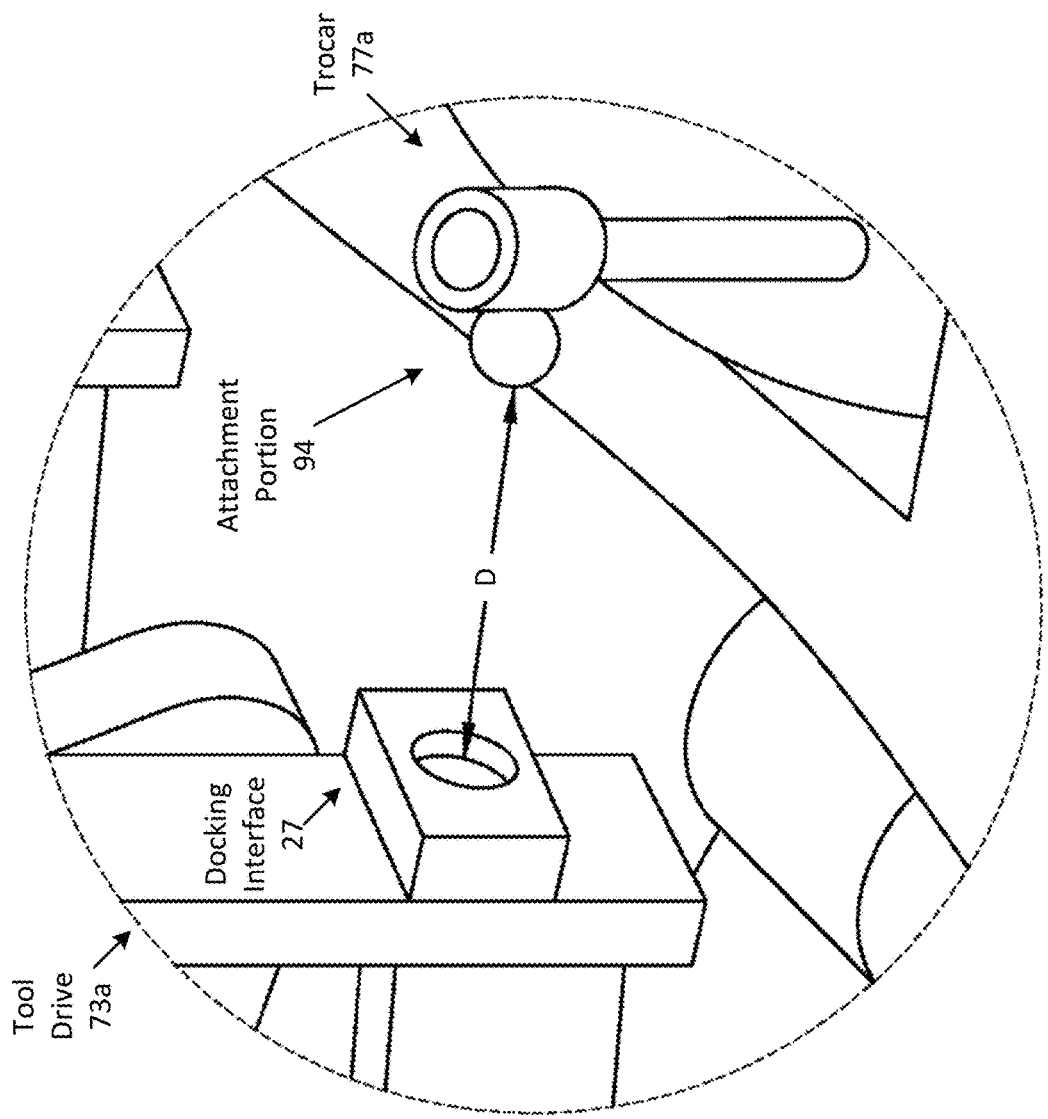

FIG. 10a illustrates each of the robotic arms in a "procedure" pose from which the operator 78 of the surgical robotic system may manually guide (e.g., while being actively assisted by the robotic arm actuators 17 under control of a processor, e.g., to augment or amplify manual forces applied by the operator) the robotic arm to couple to a trocar that is inserted into the patient. In one aspect, the procedure pose is a procedure-specific pose to maximize reach and access of the surgical workspace area while minimizing the likelihood of inter-robot collisions during teleoperation. In one aspect, the procedure pose is a predefined pose that is surgical procedure specific that is independent of anthropometric traits of patients that are to be positioned on the surgical table. In other words, the pose may be the same, regardless of the size and shape of a patient who is positioned on the table.

In one aspect, when a robotic arm is in a (predefined) procedure pose, the arm (or at least a portion of the arm) is at (or within) a threshold distance from a corresponding trocar that is coupled to a patient who is laying on the table top 75. Specifically, while each of the robotic arms is in its respective procedure pose, each of the arm's docking interface is equal to or less than a threshold distance from a corresponding trocar. For example, FIG. 10*b* is a magnified view of FIG. 10*a*, showing the docking interface 27 of tool drive 73*a* coupled to robotic arm 74*a* that is at a distance (D) from trocar 77*a*. Specifically, the docking interface 27 is within D of an attachment portion 94 of the trocar, that protrudes from the trocar and is configured to (removeably) couple to the docking interface 27. In some aspects, each of the procedure poses of the robotic arms 74*a*-74*d* may bring each of their respective tool drives 73*a*-73*d* a (same or different) distance (such as D) from a respective trocar. In other words, each robotic arm may have a corresponding procedure pose in which a respective docking interface is moved within a respective threshold distance of a respective trocar.

In another aspect, along with (or in lieu of) the docking interface being within the threshold distance, each robotic arm's procedure pose may maximize distances between other robotic arms (and/or other objects within the surgical room). For example, the links 20A-20E and/or the joints 21A-21E of robotic arm 73*a* may be separated from (e.g., corresponding or different) links and joints of each other robotic arm 73*b*-73*d* as much as possible. This may ensure that each of the robotic arms has sufficient space between other robotic arms in order to prevent arms from bunching up.

In another aspect, the procedure pose may correspond to a pose of a portion of the robotic arm. For example, the procedure pose of robotic arm 74*a* is a pose of (e.g., a docking interface of) tool drive 73*a* (position and/or orientation) that at least partially matches a pose of a corresponding trocar, which in this case would be trocar 77*a*. In some aspects, the pose of the tool drive 73*a* and the trocar 77*a* may at least partially match, while the tool drive is positioned at the distance, D, described above. As described herein, once in this pose the operator may manually guide the robotic arm the rest of the way to latch the tool drive to the trocar.

In one aspect, the surgical robotic system may include other poses not illustrated herein. For example, at least one of the robotic arms may be in a "stow" pose, in which the robotic arm is in a folded configuration and stowed under the table top 75 of the surgical table 5. While each of the arms are in this pose, patients may access (e.g., lay on) the surgical table without bumping into or colliding with the arms. In one aspect, each of the robotic arms may be positioned in the stow pose before and/or after each surgical procedure.

In one aspect, the robotic arms may transition between one or more of these poses while the surgical robotic system drive (e.g., one or more actuators of) the arms along a planned trajectory that is associated with a surgical procedure to a procedure pose. More about each of the poses illustrated in FIGS. 7-10*b* and the robotic arms transition between the poses while being driven along planned trajectories is described herein.

Figure 3:
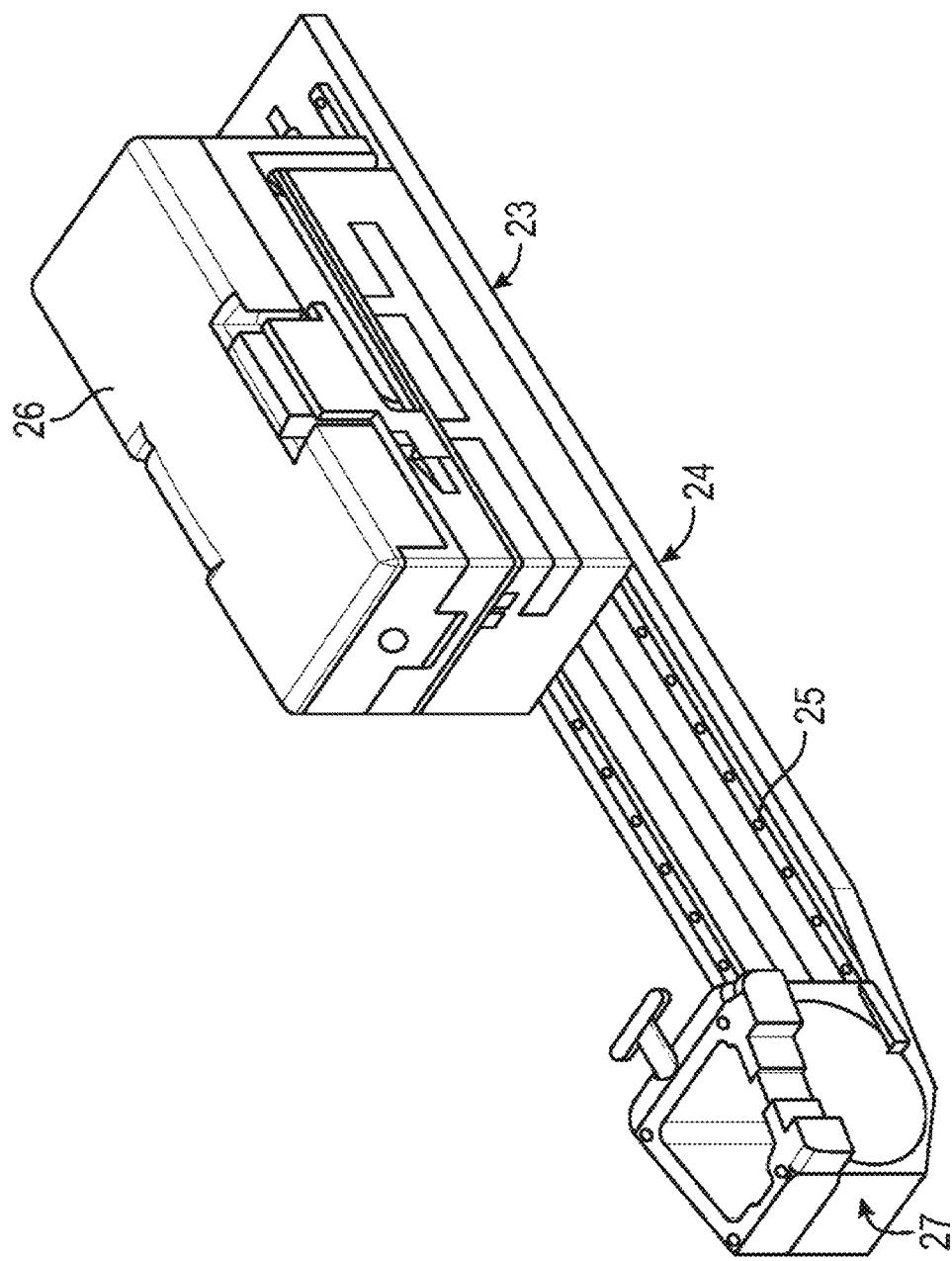
FIG. 3 is a schematic perspective view of a tool drive of the robotic arm of FIG. 2.

FIG. 3 is a schematic diagram illustrating an exemplary tool drive 23 without a loaded tool in accordance with aspects of the subject technology. In one aspect, the tool drive 23 may include an elongated base (or "state") 24 having longitudinal tracks 25 and a tool carriage 26, which is slidingly engaged with the longitudinal tracks 25. The stage 24 may be configured to couple to a distal end of a robotic arm 4 such that articulation of the robotic arm 4 positions and/or orients the tool drive 23 in space. The tool carriage 26 may be configured to receive a tool for extending through a trocar.

Additionally, the tool carriage 26 may actuate a set of articulated movements through a cable system or wires manipulated and controlled by actuated rives (the terms "cable" and "wire" are used interchangeably throughout this application). The tool carriage 26 may include different configurations of actuated drives, such as a mechanical transmission.

Figure 4:
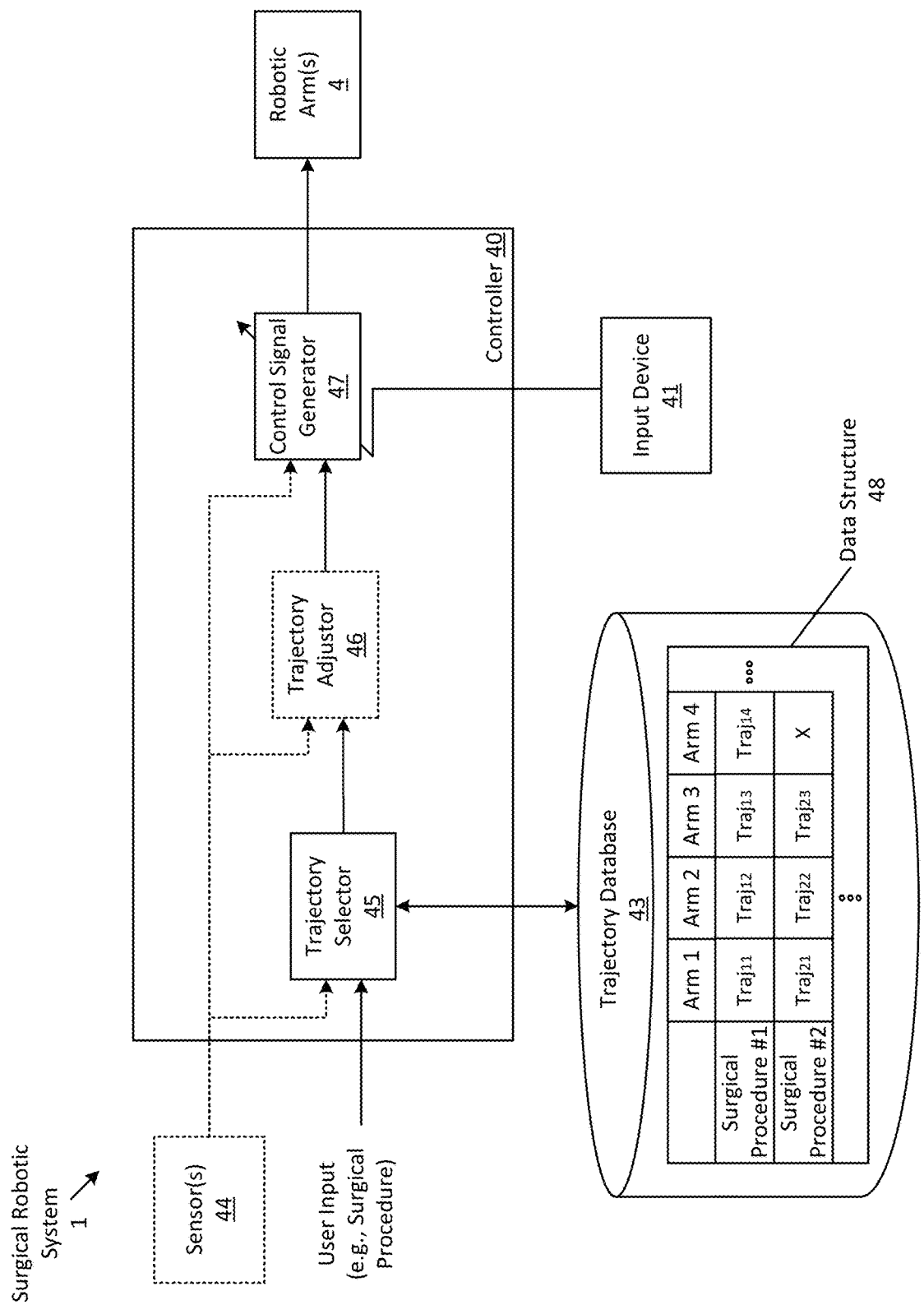
FIG. 4 is a block diagram of the surgical robotic system according to one aspect.

FIG. 4 is a block diagram of the surgical robotic system 1 that performs a robot-assisted setup for surgical procedures according to one aspect. The block diagram includes a controller 40, an input device 41, a trajectory database (or storage) 43, one or more sensors 44, and one or more robotic arms 4. In one aspect, the system 1 may include more or less components. For example, the system may include two or more input devices, or the system may not include sensors.

In one aspect, the sensor 44 may be any type of sensor that is arranged to sense (or detect) environmental characteristics in or around the operating room (e.g., as illustrated in FIG. 1), and is configured to generate sensor data (e.g., as electrical signals) that indicates such characteristics. For example, the sensor may be an optical sensor, such as a camera that is arranged to capture image data of a scene within a field of view of the camera as one or more images. Specifically, the camera's field of view may include at least a portion of the surgical table 5, one or more of the robotic arms 4, and/or an area surrounding the table and arms. In one aspect, the camera may be a three-dimensional (3D) camera that is configured to capture images and render them in 3D, providing realistic depth. As another example, the sensor may include a motion sensor that is arranged to sense motion (e.g., of a user, of one or more robotic arms, etc.), and is configured to produce motion data that represents such motion. In another aspect, the sensor may include a proximity sensor (e.g., an inductive sensor, a capacitive sensor, etc.) that is configured to detect the presence or absence of objects. In another aspect, the sensor may be a microphone that is arranged to capture ambient sounds as a microphone signal.

In one aspect, at least some of the sensors 44 may be separate electronic devices that are positioned about the operating room, or more specifically, about the surgical table 5, as illustrated in FIG. 1. In another aspect, at least some of the sensors may be a part of one or more components, such as the surgical table and one or more of the robotic arms. For instance, the robotic arms 4 may include one or more sensors, such as a force/torque (F/T) sensor that is configured to receive, as inputs, forces or torques that have been manually exerted, on the robotic arm 4 by an operator (or an object, such as another robotic arm that comes into contact with a robotic arm that includes the F/T sensor), and to produce corresponding electrical signals as outputs (e.g., to the controller 40). The F/T sensor can also receive, as inputs, forces excreted on the robotic arm by the robotic arm actuators 17. Accordingly, the F/T sensor can be configured to receive, as inputs, linear forces or rotational forces, e.g., torque. In one aspect, one or more F/T sensors may be mounted or integrated in one or more portions (e.g., one or more joints and/or one or more links) that make up the robotic arm 4. In another aspect, the robotic arm may include sensors that indicate the position and/or orientation of at least a portion of the robotic arm. For instance, the arm may include a motion sensor (e.g., an inertial measurement unit (IMU) that is configured to measure (or sense) motion and/or orientation of at least a portion of the robotic arm, and generate sensor data that indicates the motion (or position) and orientation of the arm. In another aspect, the arm may include proximity sensors that indicate the position of the arm (e.g., with respect to other objects and/or other portions of the robotic arm).

In one aspect, the input device 41 may be any type of electronic device that is configured to communicatively couple to the controller 40 and receive user input. For example, the input device may be a computer with one or more input peripheral devices, such as a mouse, keyboard, touch-sensitive display screen, etc. In another aspect, the input device may be a portable electronic device, such as a tablet computer, a laptop, a smart phone, or a remote controller. In one aspect, the input device 41 may be configured to establish a communication link with the controller 40 in order to exchange data. For example, the link may be a wired link (e.g., via optical fiber) and/or a wireless link, using any wireless protocol. As illustrated in FIGS. 7-10a, the input device 41 (which is illustrated as a tablet computer) may be located (and held by the operator 78) in the operating room. In another aspect, the input device may be at another location remote from the operating room (and from the surgical table).

The trajectory database 43 is a storage (e.g., memory) that stores, for one or more (predefined) surgical procedures, one or more planned trajectories for one or more of the robotic arms 4 of the surgical robotic system. As described herein, a planned trajectory includes a path along which (e.g., a portion of) a robotic arm moves and is orientated by the surgical robotic system, or more specifically by one or more actuators 17 of the robotic arm, in order to automatically (e.g., without user intervention) drive the arm from a first (e.g., current) to a second (e.g., procedure) pose. For example, a planned trajectory may define a path along which a (docking interface 27 of a) tool drive 23 coupled to a distal end of a robotic arm 4 moves from one position in space to another position. In one aspect, the first pose from which a robotic arm begins to traverse along the path may be a predefined pose, such as the stow pose, or the drape pose illustrated in FIG. 7. In another aspect, the current pose may be any pose that may be formed by the robotic arm.

In one aspect, a planned trajectory may include a series (or sequence) of poses that a robotic arm can reach (e.g., within a defined range of motion), including a determined duration between each pose, which is based on a speed at which the (e.g., actuators 17 of the) robotic arm moves. For instance, when robotic arm 74a is driven along a planned trajectory that starts at the drape pose illustrated in FIG. 7, the arm may subsequently be repositioned and/or re-orientated into the candle pose illustrated in FIG. 8, then the preparation pose illustrated in FIG. 9, and finally into the procedure pose illustrated in FIG. 10a.

In some aspects, the planned trajectories may be predefined paths in which while one or more of the robotic arms are driven along respective planned trajectories (either consecutively or simultaneously), no portion of the robotic arm comes into contact with 1) at least 95% of patients who may be positioned on the table top 75 of the surgical table 5 for a surgical procedure associated with the planned trajectory, 2) any other portion of other robotic arms of the surgical robotic system, 3) and other objects that are within a range of motion of the robotic arm, such that the robotic arm does not collide with other arms, the patient, or objects while being driven along the planned trajectory. In one aspect, the planned trajectories may be predefined to avoid collisions. More about predefining the planned trajectories is described herein.

As illustrated, the database 43 includes a data structure 48 that associates, for each surgical procedure, one or more planned trajectories that may be used (by the surgical robotic system) to drive one or more of the robotic arms to respective procedure poses. In particular, the data structure includes planned trajectories for at least four robotic arms (e.g., arms 74a-74d, as illustrated in FIG. 7). For instance, for the first surgical procedure, the data structure includes a trajectory for each of the four arms. In one aspect, each of the trajectories ($Traj_{11}$-$Traj_{14}$) may be a different path for a respective robotic arm (or a portion of the robotic arm) to move and orientate in order to arrive at a respective procedure pose. For the second surgical procedure, the data structure includes a planned trajectory for the first three arms ($Traj_{21}$-$Traj_{23}$), while not having a trajectory for the fourth arm (represented as an "X"). In this case, the second procedure may only require three of the four arms, and therefore the fourth arm may remain in one pose (e.g., a stowed pose) while the other three are moved according to their respective planned trajectories.

In one aspect, each arm may be associated with one or more trajectories for a given surgical procedure. In particular, for the first surgical procedure, the data structure 48 may include several planned trajectories for arm 1, each planned trajectory starting from a different pose to the (same) predefined procedure pose and/or having a different path from one pose to another. For example, the data structure may include at least three planned trajectories, each starting at one of the poses illustrated in FIGS. 7-9, while each of the planned trajectories may end (or result) in the procedure pose illustrated in FIG. 10a. In another aspect, the at least some of the trajectories for a given arm may include different procedure poses.

In some aspects, the controller 40 may be a special-purpose processor such as an application-specific integrated circuit (ASIC), a general purpose microprocessor, a field-programmable gate array (FPGA), a digital signal controller, or a set of hardware logic structures (e.g., filters, arithmetic logic units, and dedicated state machines). In one aspect, the controller may be a part an electronic device, such as the console computer system 16, the control tower 3, and/or the input device 41. Although illustrated as being a single component, in one aspect the controller may comprise one or more electronic components (e.g., processors) that are communicatively coupled on a single electronic device (such as the console computer 16), or across multiple devices (e.g., communicating over a wireless computer network). In some aspects, the controller may be a part of a separate device, such as a part of a remote server that is in communication with one or more electronic devices.

As described herein, the controller is configured to perform robot-assisted setup operations for the surgical robotic system 1. In one aspect, operations performed by the controller may be implemented in software (e.g., as instructions) stored in memory of the surgical robotic system (and/or stored in memory of the controller) and executed by the controller and/or may be implemented by hardware logic structures. As illustrated, the controller 40 may have one or more operational blocks, which may include a trajectory selector 45, a trajectory adjustor 46, and a control signal generator 47.

The operations performed by the (e.g., operational blocks of the) controller 40 to perform robot-assisted setup operations will now be described. The trajectory selector 45 is configured to select one or more planned trajectories based on a surgical procedure that is to be performed by the surgical robotic system 1. In one aspect, the selector is configured to determine a surgical procedure that is to be performed using several robotic arms (e.g., arms 74a-74d illustrated in FIG. 7) of the surgical robotic system 1. Specifically, the selector receives user input indicating a (e.g., user-selected) surgical procedure. The user input may be received via any electronic device that is communicatively coupled to the controller, such as the input device 41. For example, the input device may include a display screen on which a graphical user interface (GUI) is displayed that includes one or more GUI items, each associated with a different surgical procedure, such as a gastrectomy, a gastric bypass, and a cholecystectomy. The user input may be received in response to a user selection of a GUI item. In another aspect, the determined surgical procedure may be based on a user selection of a patient file (e.g., within a patient file system), which indicates what surgical procedure the surgical robotic system is to perform upon the patient.

The trajectory selector 45 is configured to determine (or select) a planned trajectory for at least one of the robotic arms based on the surgical procedure, each of the planned trajectories being from a current respective pose of the robotic arm to a predefined procedure pose, as described herein. For instance, the trajectory selector may perform a table lookup into the data structure 48 stored within the trajectory database 43 that associates each of one or more surgical procedures with one or more planned trajectories for one or more of the robotic arms, as describe herein. Specifically, the selector may use the determined surgical procedure to perform the table lookup to determine whether there is a matching procedure within the data base. Upon determining that there is a matching procedure, the selector may select trajectories for the procedure that are associated with the arms of the surgical system.

In one aspect, the trajectory selector 45 may be configured to use sensor data generated from one or more sensors 44 and/or input data to perform the planned trajectory selection. For example, the selector may use sensor data to determine a current pose of a robotic arm, and select the planned trajectory from the data structure that begins at (or includes) the determined pose. In one aspect, the sensor data may include data (or signals) received from one or more F/T sensors or motion sensors, which indicate a current pose of a robotic arm. In another aspect, the selector may determine the current pose based on image data captured by one or more cameras. In another aspect, the selector may determine the current pose based on input data, for example the user may input the current pose of the robotic arm via the input device 41. In another aspect, the selector may determine a current pose of a robotic arm based on a log (e.g., stored in memory) of prior movements and/or orientations of the arm.

When a planned trajectory does not begin at the current pose, but includes the current pose, the selector may select a portion of the planned trajectory (e.g., that starts at the current pose and ends at the procedure pose).

In one aspect, the trajectory selector may perform the planned trajectory selection based on user input. For example, the user input may indicate which of the robotic arms are to be driven along a planned trajectory. For example, a user may select (e.g., via a GUI displayed on the input device 41) two robotic arms (e.g., arms 74a and 74b illustrated in FIG. 7) to be driven along respective planned trajectories. In another aspect, the user may select a destination or ending pose at which a robotic arm is to stop at the end of a planned trajectory, rather than stopping at the procedure pose, as described herein. In this case, a user may select a robotic arm to be driven to a different pose, such as the poses illustrated in FIGS. 7-9.

The trajectory adjustor 46 is configured to adjust one or more of the selected planned trajectories. Specifically, the adjustor is configured to receive one or more selected planned trajectories from the selector 45, and is configured to determine whether any of the selected planned trajectories are to be adjusted. As described herein, a planned trajectory may be a predefined path along which a robotic arm moves such that no portion of the arm collides with another object, such as another arm or a portion (e.g., arm rest) of the surgical table. Since these trajectories are predefined, the adjustor may determine whether an object (e.g., either not accounted for while the planned trajectory was defined or an object that although accounted for has moved and) is now within the path of a planned trajectory of at least a portion of the robotic arm. For example, the trajectory adjustor may receive sensor data that describes aspects of the surgical environment, such as the position of objects, and from the sensor data determine whether an object is obstructing (or will obstruct) an arm's path. In particular, the adjustor may receive an image captured by one or more cameras of the surgical robotic system. For instance, the input device 41 (which is being held by the operator 78, as shown in FIG. 7), may include a camera that captures an image of at least a portion of the operating room, which may include a portion of a robotic arm. In one aspect, the camera may be a 3D camera that is configured to capture 3D images, as described herein. If the adjustor determines that there is an object within a planned trajectory, the adjustor is configured to adjust the trajectory, such that the path is clear of any objects or potential collisions. In one aspect, the adjustor may take into account other planned trajectories while adjusting one or more trajectories, such as assuring that the adjusted trajectory does not interfere with another trajectory of another robotic arm. In one aspect, the adjustor may adjust planned trajectories, while the predefined procedure pose at which the planned trajectory ends remains the same.

The control signal generator 47 is configured to signal one or more robotic arms to drive (or control) the arms along their respective planned trajectories. In particular, the generator is configured to receive planned trajectories from the selector 45 and/or adjusted planned trajectories from the adjustor 46, and is configured to generate control signals to drive the robotic arms 4 along their respective planned trajectories from their respective current pose to a respective predefined procedure pose. In one aspect, the controller 40 may simultaneously (or consecutively) drive each of the robotic arms along their respective planned trajectories to respective predefined procedure poses. In one aspect, the controller 40 uses the control signals generated by the generator 47 to signal one or more actuators 17 of one or more robotic arms 4 to drive a segment, joint, or link of the arm to move and/or orientate according to an arm's respective planned trajectory. Once a robotic arm is positioned and orientated into its respective procedure pose, the controller may pause the arm in place.

In one aspect, the generator 47 is configured to receive sensor data from one or more sensors 44, and is configured to drive the robotic arms based on the sensor data. For example, while driving (e.g., signaling at least one actuator of) a robotic arm to traverse a planned trajectory, the generator may pause the robotic arm if sensor data indicate that an object is going to (or has) collided with the arm. As described herein, one or more sensors (e.g., F/T sensors) may be integrated within the robotic arms. While a robotic arm is being driven along its planned trajectory, F/T sensors (or contact sensors) may sense and generate data (signals) upon the arm coming into contact with an object. Upon determining that the arm is in contact with an object, the generator may pause the arm and/or reverse the arm along the planned trajectory in order to avoid any further contact. In another aspect, upon determining that an arm is going to come into contact with an object, the trajectory adjustor may adjust a planned trajectory (e.g., in real time), in which case the generator may adjust the movement of the robotic arm in order to avoid collisions. In another aspect, the sensor data may include one or more images captured by one or more cameras of the surgical robotic system. Upon determining that an arm is going to come into contact with an object within the image, the generator may pause the arm.

In some aspects, the generator 47 may be configured to signal the robotic arms 4 to traverse along their respective planned trajectories based on user input at the input device 41. For instance, the input device includes an input 79, which is illustrated in FIG. 7 as a physical input, such as a button or switch. In one aspect, the input may be a GUI item displayed on a (e.g., touch-sensitive) display screen of the input device. When the input is selected (and held) by an operator, the input device is configured to generate a control signal that controls the operation of the generator 47. In particular, while the input device generates the control signal in response to the input being held by the operator, the generator 47 may (continue) to produce control signals and the controller may continue driving the robotic arms according to the control signals along their respective planned trajectories. Thus, so long as the input device receives user input, the surgical robotic system drives the robotic arms. In response to the input device not receiving user input, however, (e.g., upon a user releasing the input 79) the generator may pause each of the robotic arms at an intermediate pose between an initial pose at which the arm begins to traverse the planned trajectory and a respective predefined procedure pose. In one aspect, upon receiving user input again at the input device, the generator may continue signaling the robotic arms to traverse their planned trajectories.

In one aspect, at least some of the components and/or operations described in this figure are optional. Specifically, the surgical robotic system 1 may not include the sensors 44 and/or the controller 40 may not include the trajectory adjustor 46. In this case, the control signal generator 47 may receive the selected planned trajectories from the selector 45, and may drive the robotic arms according to the selected planned trajectories (and while the input device 41 is receiving user input). Thus, the controller 40 may not adjust planned trajectories.

Figure 5:
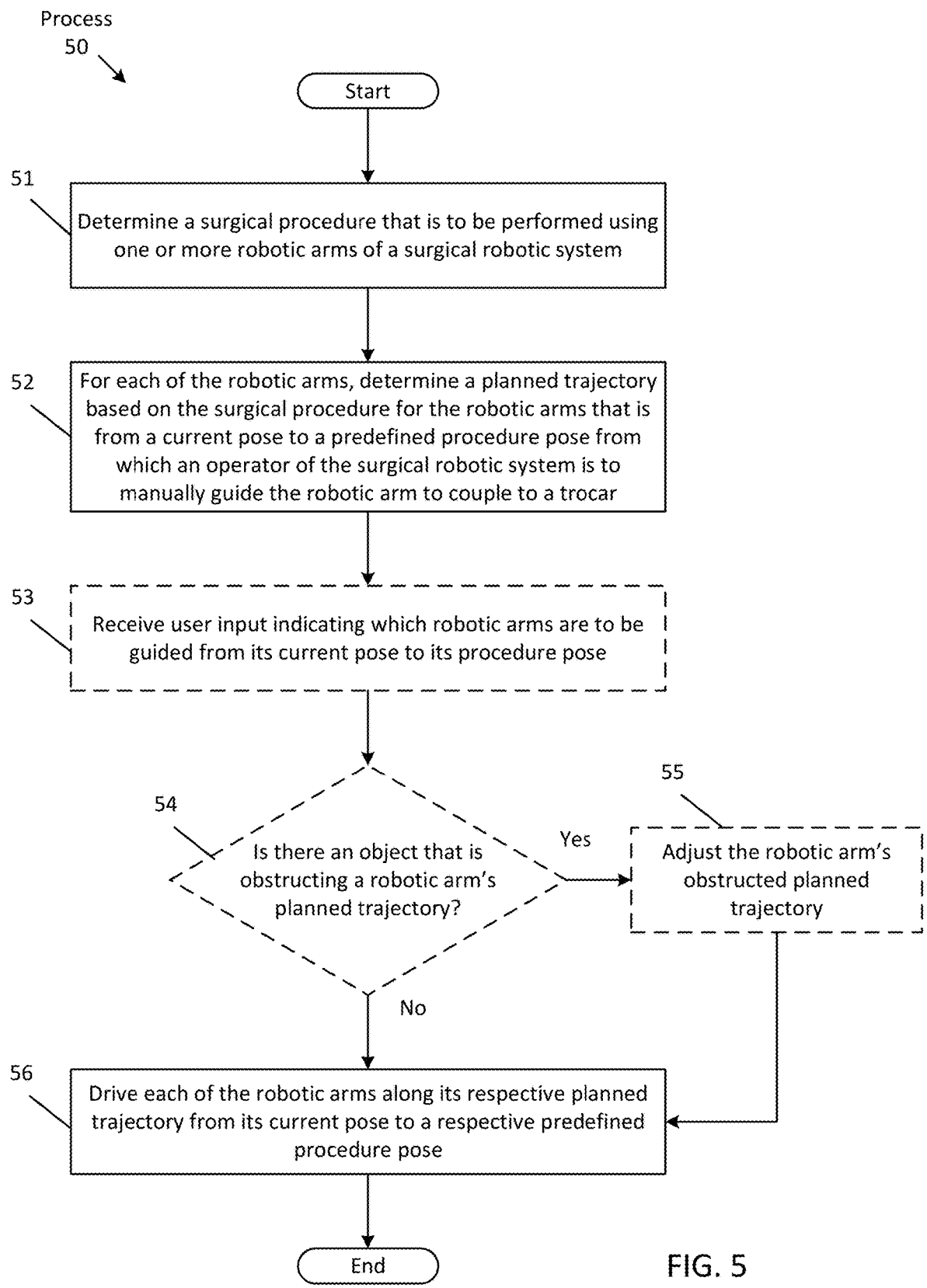
FIG. 5 is a flowchart of a process for determining and driving one or more robotic arms along planned trajectories.
Figure 6:
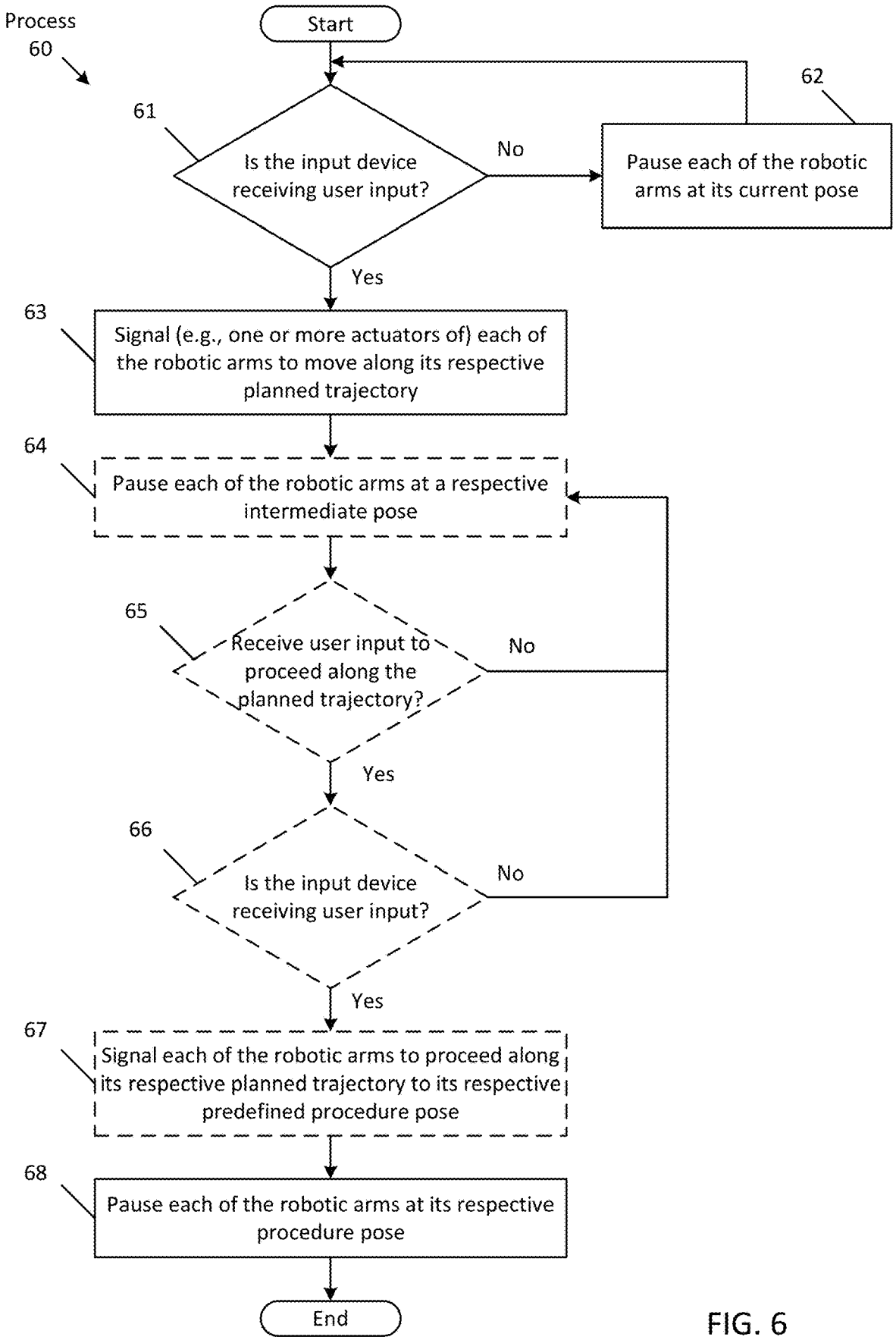
FIG. 6 is a flow chart of a process for driving one or more robotic arms along their respective planned trajectories to their respective procedure poses.
Figure 11:
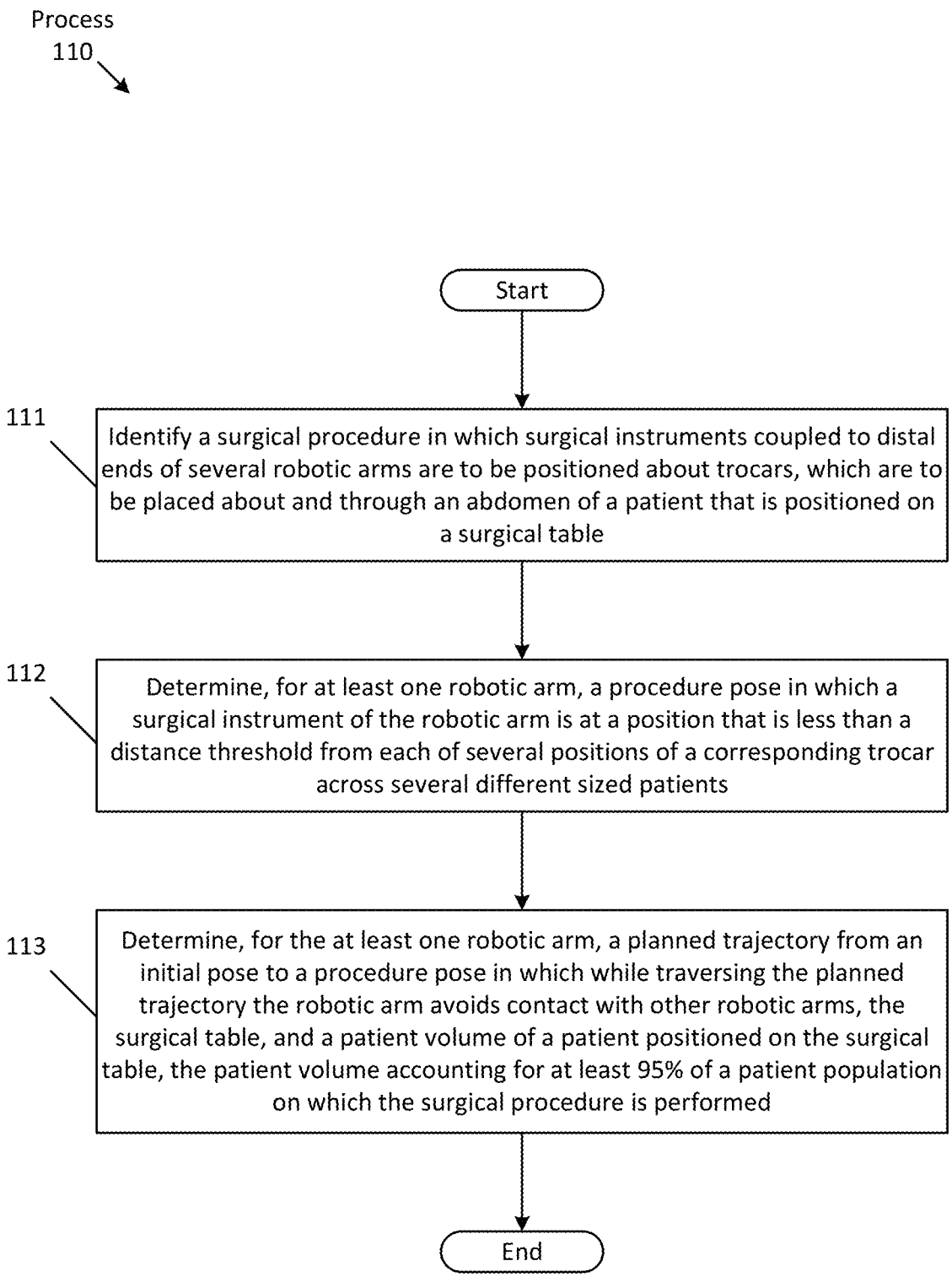
FIG. 11 is a flowchart of a process for determining planned trajectories for robotic arms.

FIGS. 5, 6, and 11 are flowcharts of processes 50, 60, and 110, respectively for performing robot-assisted setup. In one aspect, the processes are performed by the surgical robotic system 1. For instance, each of the processes may be performed by the controller 40. As another example, process 110 may be performed by (e.g., a processor of) the control tower 3 and/or user console 2. In which case, the process 110 may be performed in advance of the surgical procedure (e.g., a day, a week, a month prior). Thus, these figures will be described with reference to FIGS. 1-4.

Regarding FIG. 5, this figure is a flowchart of the process 50 for determining and driving one or more robotic arms along planned trajectories. In one aspect, prior to (or during) process 50 the patient to which the surgical procedure is to be performed may be positioned on the surgical table 5, and robotic arms of the system may be deployed from the stow pose (e.g., from under the table top) to another pose, such as the drape pose, as illustrated in FIG. 7. The process 50 begins by the controller 40 determining a surgical procedure that is to be performed using one or more robotic arms of the surgical robotic system (at block 51). For instance, an operator may input patient information within the input device 41, which may indicate a surgical procedure that is to be performed by the system upon the patient. The controller 40 determines, for each (or at least some) of the robotic arms, a planned trajectory based on the surgical procedure that is from a current pose to a predefined procedure pose from which an operator of the system is to manually guide the robotic arm to couple to a trocar (at block 52). For instance, the trajectory selector 45 may perform a table lookup into a data structure stored within the trajectory database 43, as described herein. The controller 40 receives user input indicating which robotic arms are to be driven from its current pose to its respective procedure pose (at block 53). For example, the input device 41 may display a GUI with one or more GUI items, each associated with a particular robotic arm. Upon receiving a user selection, the input device 41 may transmit signals to the controller indicating which robotic arms are selected that are to be driven to their procedure pose.

The controller 40 determines whether there is an object within the surgical environment that is obstructing a robotic arm's planned trajectory (at decision block 54). As described herein, the controller may perform this determination based on sensor data, such as images of the operating environment captured by one or more cameras. For instance, the images may include a scene of the operating room. From the image, the controller may determine whether an object, such as another robotic arm or a separate object is within an arms planned trajectory. If so, the controller 40 adjusts the robotic arm's obstructed planned trajectory (at block 55). In this case, the controller 40 may adjust the planned trajectory such that the robotic arm does not collide with another object, while the predefined procedure pose at which the trajectory ends remains the same. The controller 40 drives each of the robotic arms along its respective planned trajectory (which may be adjusted) from its current pose to a respective predefined procedure pose (at block 56).

In one aspect, at least some of the operations described in process 50 are optional, such as the operations described in blocks 53-55 are optionally performed. For example, the process may omit receiving user input indicating which robotic arms are to be guided, as described in block 53. Instead, the controller 40 may drive all of the robotic arms, or a portion of the robotic arms as indicated in the data structure stored in the trajectory database 43, as described herein. In another aspect, at least some of the operations described herein may be performed in an order other than as described herein. For instance, the controller 40 may receive the user input indicating which robotic arms are to be driven before the planned trajectories are determined, at block 52.

FIG. 6 is a flow chart of the process 60 for driving one or more robotic arms along their respective planned trajectories to their respective procedure poses. Specifically, at least some of the operations described in this process may be performed by the controller 40 when driving the robotic arms, as described in block 56 in FIG. 5. In describing this process, reference will be made to FIGS. 7-10*b*.

As described herein, the process 60 may begin while robotic arms 74*a*-74*d* are in their respective current poses, such as the drape poses that are illustrated in FIG. 7. In one aspect, however, the robotic arms may be in a different pose (e.g., stow pose), and/or some arms may be in one pose, while other arms are in another pose. The controller 40 determines whether the input device 41 is receiving user input (at decision block 61). For instance, the controller determines whether the input 79 of the input device 41 is receiving user input (e.g., whether the user is pressing and holding down the input). If not, the controller will (continue) to pause each of the robotic arms in its current pose, such as maintain the drape pose (at block 62). If, however, user input is received, as illustrated in FIG. 7, the controller 40 signals (e.g., one or more actuators 17 of) each of the robotic arms to move along its respective planned trajectory (at block 63). For instance, the surgical robotic system may drive (or move) each of the robotic arms from the drape pose illustrated in FIG. 7 to the candle pose illustrated in FIG. 8.

The controller may pause each of the robotic arms at a respective intermediate pose, which is a pose between its initial pose and its procedure pose (at block 64). For instance, the controller 40 may continue to drive each of the arms from the candle pose to the preparation pose illustrated in FIG. 9. Once each of the arms are arranged in its respective preparation pose, the controller may pause each of the arms, regardless of whether or not the input device is receiving user input (via input 79). In one aspect, the preparation pose provides a maximum physical and direct access to the patient. For instance, trocars 77*a*-77*d* may be inserted into the patient's abdomen or adjusted at this stage.

The controller 40 determines whether user input is received that indicates that the planned trajectories (of each of the robotic arms) is to proceed (at decision block 65). For instance, the operator may select a GUI item displayed on the display screen of the input device indicating that the robotic arms are to proceed. This may prevent the operator from having the robotic arms inadvertently proceed along the planned trajectories before final preparations are performed (e.g., inserting or adjusting the trocars). If not, the robotic arms remain paused. Otherwise, the controller 40 determines whether the input device is receiving input (at decision block 66). If so, the controller 40 signals each of the robotic arms to proceed along its respective planned trajectory to its respective predefined procedure pose (at block 67). The controller 40 pauses each of the robotic arms at its respective procedure pose (at block 68).

In one aspect, at least some of the operations in process 60 are optional operations. For instance, the operations described from blocks 64 through blocks 67 are optional, such that the controller 40 may signal the robotic arms to move along their respective planned trajectories from their initial poses to their respective procedure poses, without pausing or stopping (e.g., for a threshold period of time). In another aspect, operations of decision block 65 may be omitted. In this case, the controller 40 may pause the robotic arms at their respective intermediate poses at block 64, and signal the arms to continue in response to the input device receiving user input, at block 67.

FIG. 11 is a flowchart of the process 110 for determining (or developing) planned trajectories for robotic arms. Specifically, this process describes defining procedure poses and defining trajectories for arms to be driven to the procedure poses for a surgical procedure. As described herein, these operations may be performed before the surgical procedure is performed by the surgical robotic system 1.

The controller 40 identifies a surgical procedure in which tool drives (such as drive 23 illustrated in FIGS. 2 and 3) coupled to distal ends of several robotic arms are to be positioned about trocars, which are to be placed about and through (e.g., an abdomen of) a patient who is positioned on a surgical table (at block 111). In one aspect, to identify the surgical procedure, the controller may receive a user input indicating a user selection of the surgical procedure (e.g., through a user selection of a GUI item displayed on the input device 41).

The controller 40 determines, for at least one robotic arm, a procedure pose in which a tool drive of the robotic arm is at a position that is equal to or less than a (first) threshold distance from several positions of a corresponding trocar across several different sized patients (at block 112). For example, a surgical procedure such as a gastric bypass may require a trocar inserted into a specific point in a patient's abdomen. Since different patients may have different shaped abdomens (some smaller, some larger, etc.), the (e.g., attachment portions 94, as illustrated in FIG. 10*b* of those) trocars would be positioned (and/or orientated) differently. As an example, a trocar's attachment portion may be closer (e.g., at a first distance) from a center vertical axis running through the table top 75 of the surgical table for a first patient who is positioned on the table, while the attachment portion of the trocar may be further away (e.g., at a second distance larger than the first distance) from the center vertical axis for a second patient who is positioned (similarly) on the table. In one aspect, the controller may retrieve position and orientation data (e.g., as a data structure) of a trocar used across several different patients for previously performed surgical procedures. From the position and orientation data, the controller may determine the first threshold distance (e.g., with respect to at least one axis). For example, the data may indicate positions of a trocar across several previously performed surgical procedures. The controller may determine the first threshold distance to include a distance between two positions of the trocar that are furthest apart from one another with respect to each of the other positions of the trocar along an axis that runs through the center vertical axis. Thus, the first threshold distance may include the distance between the two furthest positions. In one aspect, the first threshold distance may be (e.g., slightly) greater than the distance between the two furthest positions. In one aspect, the controller may define the position of the tool drive for a given procedure pose to be at a distance from a furthest position of the trocar (e.g., a position of the trocar for a given previously performed surgical procedure that is closest to the center vertical axis with respect to the robotic arm) that is less than (or equal to) the first threshold distance. As a result of this definition, the position of the tool drive will be less than the first threshold distance from the attachment portion of the corresponding trocar for any given future patient on which the surgical robotic system performs the surgical procedure.

In another aspect, while in the robotic arm is in the procedure pose, the position of the tool drive may be less than another (second) threshold distance from a closest position of the trocar (e.g., a position of the trocar for another given previously performed surgical procedure that is furthest away from the center vertical axis with respect to the robotic arm).

In one aspect, the orientation of the tool drive (and/or the robotic arm) may be defined based on previously performed surgical procedures, as described herein. For instance, the controller may determine an average orientation of the trocar across the several previously performed surgical procedures, and define the orientation of the procedure pose based on the average orientation. In one aspect, the tool drive may have a same orientation (e.g., along at least one rotational axis) with respect to the average orientation of the trocar.

In another aspect, a procedure pose for a robotic arm is an average pose used across several previously performed surgical procedures at which the robotic is to be docked to a corresponding trocar. For example, the controller may retrieve position and orientation data of the robotic arm (as a data structure) across several previously performed surgical procedures. In one aspect, the data may indicate the position and orientation data of at least some of the robotic arm's links and joints. The controller may determine an average position and/or orientation of each of the links and joints and define the procedure pose based on the average.

In another aspect, the procedure pose may be defined according to one or more procedure poses of one or more other robotic arms. As described herein, the position and orientation of the links and joints of a robotic arm may be separated from other robotic arms (and/or other objects) as much as possible for a given procedure pose. For example, upon determining a position and orientation of a tool drive for a given robotic arm, the controller may determine the position and orientation of at least some links and at least some joints of the given robotic arm, such that the links and joints are at a maximum allowable distance (e.g., based on a given range of motion) from at least a portion of other arms/objects.

Referring back to FIG. 11, the controller 40 determines, for at least one robotic arm, a planned trajectory from an initial pose (e.g., a drape pose) to a procedure pose (e.g., the determined procedure pose) in which while traversing the planned trajectory the robotic arm avoids contact with other robotic arms, the surgical table, and a patient volume of a patient positioned on the surgical table, the patient volume accounting for at least 95% of a patient population on which the surgical procedure is performed (at block 113). In one aspect, to determine the planned trajectory, the controller may drive a virtual representation of a robotic arm in a virtual reality (VR) environment form an initial virtual pose to a virtual procedure pose without colliding with any object, such as another robotic arm, at least a portion of the surgical table, and the patient volume. Specifically, the controller may be configured to determine dimensions of the objects. For instance, the controller may obtain patient data from one or more patients on which the surgical procedure has previously been performed. Such data may include patient characteristic traits, such as height, width, patient volume, etc. The controller may obtain characteristic data of objects within the operation room, such as dimensions of the surgical table and objects that may be coupled to the surgical table, such as an arm rest that extends away from the table. The controller may obtain characteristics of one or more other robotic arms and the arms' planned trajectories. Based on this data, the controller may generate a virtual representation that includes at least one of 1) a patient whose volume is equal to or greater than 95% of the patient population 2) the surgical table and any objects that may be coupled to the table, and 3) planned trajectories of other robotic arms. From this the controller may generate a planned trajectory for a given robotic arm by driving a virtual representation of the robotic arm from a given initial pose (e.g., a drape pose) to the procedure pose, while not colliding with at least some of the virtual representations described here. In one aspect, the controller may define one or more intermediate poses along the path of the planned trajectory, such as the candle pose and the preparation pose.

Thus, the determination of the procedure pose and the planned trajectory is patient-agnostic, such that the pose and trajectories are not defined for a specific patient. Instead, the pose and trajectory are optimized to accommodate all (or most) patient sizes and weights that may be operated on by the surgical robotic system for a corresponding surgical procedure.

Some aspects may perform variations to the processes 50, 60, and/or 110 described herein. For example, the specific operations of at least some of the processes may not be performed in the exact order shown and described. The specific operations may not be performed in one continuous series of operations and different specific operations may be performed in different aspects.

As previously explained, an aspect of the disclosure may be a non-transitory machine-readable medium (such as microelectronic memory) having stored thereon instructions, which program one or more data processing components (generically referred to here as a "processor") to (automatically) perform robot-assisted setup operations, as described herein. In other aspects, some of these operations might be performed by specific hardware components that contain hardwired logic. Those operations might alternatively be performed by any combination of programmed data processing components and fixed hardwired circuit components.

While certain aspects have been described and shown in the accompanying drawings, it is to be understood that such aspects are merely illustrative of and not restrictive on the broad disclosure, and that the disclosure is not limited to the specific constructions and arrangements shown and described, since various other modifications may occur to those of ordinary skill in the art. The description is thus to be regarded as illustrative instead of limiting.

In some aspects, this disclosure may include the language, for example, "at least one of [element A] and [element B]." This language may refer to one or more of the elements. For example, "at least one of A and B" may refer to "A," "B," or "A and B." Specifically, "at least one of A and B" may refer to "at least one of A and at least one of B," or "at least of either A or B." In some aspects, this disclosure may include the language, for example, "[element A], [element B], and/or [element C]." This language may refer to either of the elements or any combination thereof. For instance, "A, B, and/or C" may refer to "A," "B," "C," "A and B," "A and C," "B and C," or "A, B, and C."

What is claimed is:

1. A method performed by a surgical robotic system, the method comprising:
   determining a surgical procedure that is to be performed using a robotic arm of the surgical robotic system;
   for the robotic arm, determining a planned trajectory based on the surgical procedure, the planned trajectory is from a current pose of the robotic arm to a predefined procedure pose that is within a threshold distance from a trocar that is coupled to a patient who is positioned on a table, wherein the predefined procedure pose of the robotic arm is predefined independent of anthropometrics of the patient, wherein the planned trajectory comprises a path along which the robotic arm is to move while no portion of the robotic arm is to come into contact with a patient volume positioned on the table for the surgical procedure, wherein the patient volume is at least equal to a largest volume of 95% of a patient population on which the surgical procedure has been performed; and driving the robotic arm along the planned trajectory from the current pose to the predefined procedure pose, wherein the predefined procedure pose is within the threshold distance such that a user is to manually couple a docking interface of the robotic arm to an attachment portion of the trocar.

2. The method of claim 1, wherein the anthropometrics comprise a size and shape of the patient who is positioned on the table.

3. The method of claim 1, wherein the surgical robotic system comprises a plurality of robotic arms to which the robotic arm belongs, wherein no portion of the robotic arm is to come into contact with other robotic arms of the plurality of robotic arms while the robotic arm is to move along the path.

4. The method of claim 1, wherein determining the planned trajectory based on the determined surgical procedure comprises performing a table lookup into a data structure that associates each of a plurality of surgical procedures with one or more planned trajectories for the robotic arm.

5. The method of claim 4, wherein the plurality of surgical procedures comprises at least a gastrectomy, a gastric bypass, and a cholecystectomy.

6. The method of claim 1, a distal end of the robotic arm is coupled to a surgical tool comprising a docking interface, wherein while the robotic arm is in the predefined procedure pose, the docking interface is at a distance from the trocar that is equal to or less than the threshold distance.

7. The method of claim 1, wherein the robotic arm is one of a plurality of robotic arms of the surgical robotic system, wherein driving the robotic arm comprises simultaneously moving each of the plurality of robotic arms along a respective planned trajectory to a respective predefined procedure pose.

8. The method of claim 1, wherein the robotic arm is one of a plurality of robotic arms of the surgical robotic system, wherein each of the plurality of robotic arms comprises a plurality of links that are coupled together by a plurality of joints, and a distal end of each of the plurality of robotic arms is coupled to a docking interface, wherein, while each robotic arm of the plurality of robotic arms is in its respective predefined procedure pose:

the docking interface of the robotic arm is at the threshold distance from a corresponding trocar, and the plurality of links and the plurality of joints of the robotic arm are separated from links and joints of each other robotic arm of the plurality of robotic arms at maximum distances according to their respective range of motions.

9. The method of claim 1 further comprising:

receiving an image captured by a camera of the surgical robotic system; and adjusting the planned trajectory based on the image, while the predefined procedure pose remains the same.

10. The method of claim 1, wherein the surgical robotic system comprises an input device, wherein the robotic arm is driven along the planned trajectory so long as the input device receives user input.

11. The method of claim 10 further comprises, in response to the input device not receiving user input, pausing the robotic arm at an intermediate pose between the current pose and the predefined procedure pose.

12. The method of claim 1, wherein determining the surgical procedure comprises receiving a user selection of a graphical user interface (GUI) item of a plurality of GUI items, each associated with a different surgical procedure and displayed on a display screen of the surgical robotic system.

13. The method of claim 1, wherein the robotic arm is a first robotic arm, wherein the surgical robotic system comprises a second robotic arm, wherein both robotic arms are mounted on the table, wherein, while both robotic arms are in their respective current poses there is a first open area between both robotic arms to access the patient on the table, wherein the method further comprises;

driving the second robotic arm while driving the first robotic arm such that both robotic arms move from their respective current poses along respective planned trajectories to intermediate poses in which there is a second open area between both robotic arms to access the patient on the table that is larger than the first open area; and pausing both robotic arms at their respective intermediate poses.

14. The method of claim 13 further comprising, in response to receiving user input, continuing to drive both robotic arms along their respective planned trajectories from their respective intermediate poses to respective predefined procedure poses.

15. The method of claim 1, wherein the planned trajectory accounts for objects within a range of motion of the robotic arm such that the robotic arm does not collide with the objects while being driven along the planned trajectory.

16. A surgical robotic system comprising:

a table;

one or more robotic arms; and a controller that is configured to:

determine a surgical procedure that is to be performed using the one or more robotic arms, determine, for each of the one or more robotic arms, a planned trajectory based on the surgical procedure, each planned trajectory is from a current pose of a robotic arm to a predefined procedure pose of the robotic arm that is within a threshold distance from a trocar that is coupled to a patient who is positioned on the table, wherein each predefined procedure pose for each of the one or more robotic arms is predefined independent of anthropometrics of the patient, wherein the planned trajectory of each of the one or more robotic arms comprises a path along which the robotic arm is to move while no portion of the robotic arm is to come into contact with a patient volume positioned on the table for the surgical procedure, wherein the patient volume is at least equal to a largest volume of 95% of a patient population on which the surgical procedure has been performed, and drive the one or more robotic arms along respective planned trajectories to respective predefined procedure poses.

17. The surgical robotic system of claim 16, wherein the anthropometrics comprise a size and shape of the patient that is positioned on the table.

18. The surgical robotic system of claim 16, wherein no portion of the robotic arm is to come into contact with other robotic arms of the one or more robotic arms while the robotic arm is to move along the path.

19. The surgical robotic system of claim 16, wherein determining the planned trajectory based on the surgical procedure comprises performing a table lookup into a data structure that associates each of a plurality of surgical procedures with one or more planned trajectories for at least one of the one or more robotic arms.

20. The surgical robotic system of claim 19, wherein the plurality of surgical procedures comprises at least a gastrectomy, a gastric bypass, and a cholecystectomy.

21. The surgical robotic system of claim 16, wherein a distal end of each of the one or more robotic arms is coupled to a surgical tool comprising a docking interface, wherein, while each of the one or more robotic arms is in its respective predefined procedure pose, each docking interface of the one or more the robotic arms is at a distance from a corresponding trocar that is equal to or less than the threshold distance.

22. The surgical robotic system of claim 16, wherein driving the one or more robotic arms comprises simultaneously moving each of the one or more robotic arms along a respective planned trajectory to a respective predefined procedure pose.

23. The surgical robotic system of claim 16, wherein each of the one or more of robotic arms comprises a plurality of links that are coupled together by a plurality of joints, and a distal end of each of the one or more robotic arms is coupled to a docking interface, wherein, while each of the one or more robotic arms is in its respective predefined procedure pose:
the docking interface of the robotic arm is at the threshold distance from a corresponding trocar, and
the plurality of links and the plurality of joints of the robotic arm are separated from links and joints of each other robotic arm of the one or more robotic arms at maximum distances according to their respective range of motions.

24. The surgical robotic system of claim 16, wherein the controller is further configured to:
receive an image captured by a camera; and
adjust at least one of the planned trajectories of the one or more robotic arms based on the image, while a corresponding predefined procedure pose remains the same.

25. The surgical robotic system of claim 16, wherein each of the one or more robotic arms is driven along a respective planned trajectory so long as an input device that is communicatively coupled to the controller receives user input.

26. The surgical robotic system of claim 25, wherein the controller is further configured to, in response to the input device not receiving user input, pause each of the one or more robotic arms at an intermediate pose between a respective current pose and a respective predefined procedure pose.

27. The surgical robotic system of claim 16, wherein determining the surgical procedure comprises receiving a user selection of a graphical user interface (GUI) item of a plurality of GUI items, each associated with a different surgical procedure and displayed on a display screen of an input device.

28. The surgical robotic system of claim 16, wherein the one or more robotic arms comprises at least two robotic arms, wherein, while each of the at least two robotic arms is in its respective current pose there is a first open area between the at least two robotic arms to access the patient who is positioned on the table, wherein driving the one or more robotic arms comprises:
moving the at least two robotic arms from their respective current poses along respective planned trajectories to intermediate poses in which there is a second open area between the at least two robotic arms to access the patient that is larger than the first open area; and
pausing the at least two robotic arms at their respective intermediate poses.

29. The surgical robotic system of claim 28, wherein the controller is further configured to, in response to receiving user input, continue to move the at least two robotic arms along their planned trajectories from their respective intermediate poses to their respective predefined procedure poses.

30. The surgical robotic system of claim 16, wherein each planned trajectory accounts for objects within a range of motion of a respective robotic arm such that the respective robotic arm does not collide with the object while being driven along its planned trajectory.

31. The surgical robotic system of claim 16, wherein the controller is further configured to:
display, on a display screen, a graphical user interface (GUI) that comprises a plurality of GUI items, each GUI item associated with a different robotic arm of the one or more robotic arms; and
receive, for each of the one or more robotic arms, a user-selection of a GUI item before at least one robotic arm is driven along its respective planned trajectory.

32. An apparatus comprising:
a processor; and
memory having instructions which when executed by the processor causes the apparatus to:
identify a surgical procedure in which tool drives coupled to distal ends of a plurality of robotic arms are to be positioned about trocars, which are to be placed about and through a patient who is positioned on a surgical table;
for each of the robotic arms,
determine a procedure pose in which a tool drive of the robotic arm is at a position that is less than a threshold distance from each of a plurality of positions of a corresponding trocar across a plurality of different sized patients; and
determine a planned trajectory from an initial pose to the procedure pose in which, while traversing the planned trajectory, the robotic arm avoids contact with other robotic arms, the surgical table, and a patient volume positioned on the surgical table, wherein the patient volume is at least equal to a larger volume of 95% of a patient population on which the surgical procedure has been performed, wherein the patient volume is larger than a volume of the patient who is positioned on the surgical table.

33. The apparatus of claim 32, wherein the determined procedure pose for each of the robotic arms is an average pose used across a plurality of previously performed surgical procedures at which the robotic arm is to be docked to the corresponding trocar.

34. The apparatus of claim 32, wherein the instructions to determine the planned trajectory comprises instructions to drive a virtual representation of the robotic arm in a virtual reality (VR) environment from an initial virtual pose to a virtual procedure pose without colliding with any object.

35. The apparatus of claim 34, wherein the any object comprises at least one of another robotic arm, at least a portion of the surgical table, and the patient volume.

* * * * *